US012712079B2

(12) United States Patent
Lazarev et al.

(10) Patent No.: US 12,712,079 B2
(45) Date of Patent: Aug. 18, 2026

(54) DIAGNOSTIC SYSTEMS AND METHODS FOR ANIMAL PATIENTS WITH GLOBAL DATA CENTER AND LOCAL AUTONOMOUS CELL

(71) Applicant: Aura Diagnostics, Inc., Petaluma, CA (US)

(72) Inventors: Alexander P. Lazarev, Lake Forest, CA (US); Delvin Tai Wai Yuk, Atherton, CA (US); Pavel Lazarev, Box Elder, SD (US)

(73) Assignee: Aura Diagnostics, Inc., Petaluma, CA (US)

( * ) Notice: Subject to any disclaimer, the term of this patent is extended or adjusted under 35 U.S.C. 154(b) by 63 days.

(21) Appl. No.: 18/500,604

(22) Filed: Nov. 2, 2023

(65) Prior Publication Data

US 2025/0149166 A1 May 8, 2025

(51) Int. Cl.
*G16H 50/20* (2018.01)
*G16H 50/70* (2018.01)

(52) U.S. Cl.
CPC ............. *G16H 50/20* (2018.01); *G16H 50/70* (2018.01)

(58) Field of Classification Search
None
See application file for complete search history.

(56) References Cited

U.S. PATENT DOCUMENTS 5,479,927 A 1/1996 Shmulewitz
5,717,733 A 2/1998 Kurbatov et al.
5,849,595 A 12/1998 Alfano et al.
(Continued)

FOREIGN PATENT DOCUMENTS

CN 105849744 A 8/2016
CN 107106998 B * 6/2018 ......... B01D 67/0013
(Continued)

OTHER PUBLICATIONS

Franke D, Jeffries C, Svergun D. "Machine Learning Methods for X-Ray Scattering Data Analysis from Biomacromolecular Solutions," Biophysical Journal, vol. 114, Issue 11, P2485-2492, Jun. 5, 2018. (Year: 2018).*

(Continued)

*Primary Examiner* — Robert A Sorey
(74) *Attorney, Agent, or Firm* — MLO, a professional corp.

(57) ABSTRACT

The techniques described herein relate to systems and methods for diagnosing diseases in animal patients. In some cases, a method includes providing a set of global data to a global data center and processing the set of global data and categorizing it into data clusters, where each data cluster corresponds to a diagnostic indicator for assessment of a physiological or pathological condition. The method can further include measuring data of a local patient using measurement equipment of a local autonomous cell and communicating the local measurement data from the local autonomous cell to the global data center. The local measurement data can be processed, and the processed local measurement data can be compared with the data clusters to determine a local diagnostic indicator for the local patient. The local diagnostic indicator can then be communicated from the global data center to the local autonomous cell.

23 Claims, 9 Drawing Sheets

(56) References Cited

U.S. PATENT DOCUMENTS

| | | | | |
|---|---|---|---|---|
| 6,175,117 | B1 | 1/2001 | Komardin et al. | |
| 6,483,891 | B1 | 11/2002 | Lazarev et al. | |
| 8,126,228 | B2 | 2/2012 | Fueyo et al. | |
| 9,529,974 | B2 * | 12/2016 | Li | G06Q 50/26 |
| 10,534,895 | B2 | 1/2020 | Ambrose et al. | |
| 11,522,703 | B1 | 12/2022 | Jain et al. | |
| 11,901,056 | B2 | 2/2024 | Neumann | |
| 12,300,370 | B2 | 5/2025 | Kohn | |
| 2003/0014418 | A1 | 1/2003 | Adler et al. | |
| 2003/0135096 | A1 * | 7/2003 | Dodds | G16B 50/40 600/300 |
| 2004/0258202 | A1 | 12/2004 | Wernick et al. | |
| 2006/0015265 | A1 | 1/2006 | Raich | |
| 2007/0032832 | A1 | 2/2007 | Feher | |
| 2008/0147554 | A1 | 6/2008 | Stevens et al. | |
| 2013/0208966 | A1 | 8/2013 | Zhao et al. | |
| 2015/0269323 | A1 | 9/2015 | Ginsburg | |
| 2015/0369759 | A1 | 12/2015 | Mazor et al. | |
| 2016/0203263 | A1 | 7/2016 | Maier et al. | |
| 2016/0235372 | A1 | 8/2016 | Schneider et al. | |
| 2017/0362585 | A1 | 12/2017 | Wang et al. | |
| 2018/0038845 | A1 | 2/2018 | Zimmermann et al. | |
| 2018/0122499 | A1 | 5/2018 | Austin et al. | |
| 2019/0046039 | A1 | 2/2019 | Ramesh et al. | |
| 2019/0113451 | A1 | 4/2019 | Weissleder et al. | |
| 2019/0271044 | A1 | 9/2019 | Stephan et al. | |
| 2020/0098476 | A1 | 3/2020 | Loscutoff et al. | |
| 2020/0160980 | A1 * | 5/2020 | Lyman | G06F 18/217 |
| 2020/0242760 | A1 | 7/2020 | Holmes | |
| 2022/0008027 | A1 | 1/2022 | Lazarev et al. | |
| 2022/0013227 | A1 | 1/2022 | Lazarev et al. | |
| 2022/0013233 | A1 | 1/2022 | Lazarev et al. | |
| 2022/0399126 | A1 * | 12/2022 | John | G06N 20/00 |
| 2022/0415505 | A1 | 12/2022 | Lazarev et al. | |
| 2023/0113064 | A1 | 4/2023 | Yuk et al. | |
| 2023/0240635 | A1 | 8/2023 | Lazarev et al. | |
| 2023/0270396 | A1 | 8/2023 | Lazarev et al. | |
| 2023/0341340 | A1 | 10/2023 | Lazarev et al. | |
| 2024/0000412 | A1 | 1/2024 | Lazarev et al. | |
| 2024/0016462 | A1 | 1/2024 | Lazarev et al. | |
| 2024/0161893 | A1 | 5/2024 | Lazarev et al. | |
| 2025/0149170 | A1 * | 5/2025 | Lazarev | G16H 50/20 |

FOREIGN PATENT DOCUMENTS

| | | | | | |
|---|---|---|---|---|---|
| CN | 110400617 | A | | 11/2019 | |
| CN | 112951416 | A | * | 6/2021 | |
| CN | 113012823 | A | | 6/2021 | |
| CN | 113533399 | A | * | 10/2021 | G01J 5/00 |
| CN | 114599407 | A | * | 6/2022 | C07K 14/77 |
| CN | 115769069 | A | * | 3/2023 | A61B 6/4035 |
| JP | H0933700 | A | | 2/1997 | |
| KR | 20180076702 | A | | 7/2018 | |
| WO | WO-2004071295 | A1 | * | 8/2004 | A61B 5/0006 |
| WO | WO-2005112752 | A1 | * | 12/2005 | G01N 23/20 |
| WO | WO-2012048000 | A2 | * | 4/2012 | A61B 6/4447 |
| WO | WO-2013131156 | A1 | * | 9/2013 | A61B 5/0006 |
| WO | WO-2018081884 | A1 | * | 5/2018 | A41D 1/005 |
| WO | 2019157214 | A2 | | 8/2019 | |
| WO | 2021222866 | A1 | | 11/2021 | |
| WO | 2021257451 | A1 | | 12/2021 | |
| WO | 2021257457 | A1 | | 12/2021 | |

OTHER PUBLICATIONS

Ahmadian et al., "Monitoring of drug resistance towards reducing the toxicity of pharmaceutical compounds: Past, present and future", Journal of Pharmaceutical and Biomedical Analysis, Mar. 19, 2020, 12 pgs.

Alfenaar, et al., "Therapeutic Drug Monitoring in Non Tuberculosis Mycobacteria Infections", Clinical Pharmacokinetics, Mar. 10, 2021, 15 pgs.

Arboleda et al., Assessing lesion malignancy by scanning small-angle X-ray scattering of breast tissue with microcalcifications, Phys Med Biol. Aug. 7, 2019;64(15):155010, pp. 1-9.

Buclin et al., "The Steps to Therapeutic Drug Monitoring: A Structured Approach Illustrated With Imatinib", Frontiers in Pharmacology, vol. 11, Article 177, Mar. 3, 2020, 10 pgs.

Chapman et al., Diffraction enhanced x-ray imaging, Phys. Med. Biol. 42, Nov. 1997, pp. 2015-2025.

Conceicao et al., Analysis of breast cancer by small angle X-ray scattering (SAXS), Analyst, Apr. 2009 134(6):1077-82.

European Search Report dated May 24, 2024 for European Patent Office Patent Application No. 21826535.3.

Fagundes et al., "Structural characterization of canine mammary tissue by x-ray diffraction", Radiation Physics and Chemistry, vol. 155, pp. 22-25. (Year: 2019).

Ghammraoui et al., "Maximum-likelihood estimation of scatter components algorithm for x-ray coherent scatter computed tomography of the breast", Physics in Medicine & Biology, vol. 61, pp. 3164-3179. (Year: 2016).

Ghiculescu, "Therapeutic drug monitoring: which drugs, why, when and how to do it", Australian Prescriber, vol. 31, No. 2, Apr. 2008, pp. 42-44.

Graewet et al., "Impact and progress in small and wide angle X-ray scattering (SAXS and WAXS)", Current Opinion in Structural Biology, vol. 23, pp. 748-754. (Year: 2013).

Iacuzzi et al., "Dried Blood Spot Technique Applied in Therapeutic Drug Monitoring of Anticancer Drugs: a Review on Conversion Methods to Correlate Plasma and Dried Blood Spot Concentrations", Pharm Res, Springer, Apr. 12, 2021, 20 pgs.

James, "A Review of Low Angle Fibre Diffraction in the Diagnosis of Disease", British Journal of Medicine & Medical Research, 3(2): 383-397, Feb. 19, 2013.

James, "Fiber diffraction of skin and nails provides an accurate diagnosis of malignancies", Int. J. Cancer: 125, 133-138, 13 pages, Jul. 2009.

Kuwayama et al., "Time-course measurements of drug concentrations in hair and toenails after single administrations of pharmaceutical products", Drug Testing and Analysis, Jun. 24, 2016, 7 pgs, John Wiley & Sons, Ltd.

Lupien et al., "Effects of stress throughout the lifespan on the brain, behaviour and cognition", Focus on Stress, Jun. 2009, 12 pgs, Macmillan Publishers Limited.

Moss et al., Correlation of X-ray diffraction signatures of breast tissue and their histopathological classification, Scientific Reports, Oct. 2017, pp. 1-9.

Notice of Allowance and Fees dated Feb. 6, 2023 for U.S. Appl. No. 17/593,846.

Notice of Allowance and Fees dated Jul. 19, 2023 for U.S. Appl. No. 17/448,888.

Notice of Allowance and Fees dated May 20, 2024 for U.S. Appl. No. 17/448,886.

Office Action dated Feb. 26, 2024 for U.S. Appl. No. 17/448,886.

Office Action dated Mar. 22, 2023 for U.S. Appl. No. 17/448,888.

Oliver et al., Diffraction enhanced imaging utilizing a laser produced x-ray source, Rev. Sci. Instrum. 93, 093502, Sep. 2022, 7 pages.

Ong et al., "Optical biosensors—Illuminating the path to personalized drug dosing", Biosensors and Bioelectronics, May 13, 2021, 21 pgs.

Ortiz et al., "Biomarkers of disease in human nails: a comprehensive review", Critical Reviews in Clinical Laboratory Sciences, Oct. 7, 2021, 18 pgs, Taylor & Francis Group.

Park, Hye Lyun, Authorized Officer, Korean Intellectual Property Office, "International Search Report" in connection with related International Application No. PCT/US2021/037238, dated Oct. 5, 2021, 5 pgs.

Park, Hye Lyun, Authorized Officer, Korean Intellectual Property Office, "Written Opinion of the InternationalSearching Authority" in connection with related International Application No. PCT/US2021/037238, dated Oct. 5, 2021, 5 pgs.

Rodriguez, Kari, Authorized Officer, Commissioner for Patents, "International Search Report" in connection with related International Application No. PCT/US2021/037224, dated Sep. 29, 2021, 3 pgs.

(56) References Cited

OTHER PUBLICATIONS

Rodriguez, Kari, Authorized Officer, Commissioner for Patents, "Written Opinion of the International Searching Authority" in connection with related International Application No. PCT/US2021/037224, dated Sep. 29, 2021, 6 pgs.
Round et al., A preliminary study of breast cancer diagnosis using laboratory based small angle x-ray scattering, Phys Med Biol. Sep. 2005, 50(17):4159-68.
Sidhu et al., Mapping structural changes in breast tissue disease using x-ray scattering, Medical Physics 36, May 2009, pp. 3211-3217.
Todd et al., "Survival in dementia and predictors of mortality: a review", International Journal of Geriatric Psychiatry, Mar. 2013, 16pgs, John Wiley & Sons, Ltd.
Visser, "Techniques for Monitoring Drug Efficacy", Vet Clin North Am Exot Anim Pract., 21(2), May 2018, 287-295, 2018, 7pgs.
Wallenburg et al., "Personalised antimicrobial dosing: standing on the shoulders of giants", International Journal of Antimicrobial Agents, Sep. 2020, 18 pgs.
Wiencek, et al., "Rapid Assessment of Drugs of Abuse", Advances in Clinical Chemistry, Dec. 2016, 33 pgs, Elsevier Inc., Nashville, TN.
Yoneyama et al., Fast diffraction-enhanced imaging using continuous sample rotation and analyzer crystal scanning, J Synchrotron Radiat, Mar. 2020, pp. 468-471.
Zheng et al., "Recent advances in drug release monitoring", Nanophotonics, 8(3), Feb. 2009, pp. 391-413.
European Search Report dated Dec. 4, 2024 for United Kingdom Patent Application No. 2410187.5.
European Search Report dated Dec. 5, 2024 for United Kingdom Patent Application No. 2410185.9.
International Search Report and Written Opinion dated Jan. 17, 2025 for PCT Patent Application No. PCT/IB2024/059571.
International Search Report and Written Opinion dated Jan. 23, 2025 for PCT Patent Application No. PCT/IB2024/060284.
International Search Report and Written Opinion dated Jan. 23, 2025 for PCT Patent Application No. PCT/IB2024/060286.
International Search Report and Written Opinion dated Jan. 31, 2025 for PCT Patent Application No. PCT/IB2024/060287.
Frolov et al., "Risk stratification personalised model for prediction of life-threatening ventricular tachyarrhythmias in patients with chronic heart failure," Kardiologia Polska Mar. 2017; 75, 7: 682-688; DOI: 10.5603/KP.a2017.0060.
James, "Fiber diffraction of skin and nails provides an accurate diagnosis of malignancies", Int. J. Cancer: 125, Feb. 2009, pp. 133-138.
Lazarev et al., "Human Tissue X-ray Diffraction: Breast, Brain, and Prostate", Proceedings of the 22nd Annual International Conference of the IEEE Engineering in Medicine and Biology Society, Cat. No. 00CH37143, vol. 4, Jul. 2000, pp. 3230-3233.
Ortin et al., "Automated real-time method for ventricular heartbeat classification," Computer Methods and Programs in Biomedicine 169 (2019) 1-8, Nov. 2018, 8 pages.
Wang et al., "A High Precision Real-time Premature Ventricular Contraction Assessment Method based on the Complex Feature Set," Journal of Medical Systems (2020) 44:3, published Nov. 2019, 16 pages.
Wu et al., "ECG signal classification with binarized convolutional neural network," Computers in Biology and Medicine 121, 103800, May 2020, 9 pages.
Office Action dated Apr. 8, 2025 for U.S. Appl. No. 18/500,624.
Office Action dated Jun. 16, 2025 for U.S. Appl. No. 18/298,190.
Office Action dated Jun. 16, 2025 for U.S. Appl. No. 18/298,218.
Office Action dated Jul. 25, 2025 for U.S. Appl. No. 18/352,085.
Office Action dated Jul. 25, 2025 for U.S. Appl. No. 18/352,094.
Notice of Allowance and Fees dated Apr. 14, 2026 for U.S. Appl. No. 18/500,616.
Notice of Allowance and Fees dated Mar. 5, 2026 for U.S. Appl. No. 18/827,367.
Arboleda et al., "Assessing lesion malignancy by scanning small-angle X-ray scattering breast tissue with microcalcifications", Physics in Medicine, and Biology, vol. 64, No. 15, pp. 1-9, Dec. 31, 2019.
Office Action dated Feb. 9, 2026 for China Patent Application No. 202180042558.4.
Sidhu et al., "Classification of breast tissue using a laboratory system for small-angle x-ray scattering (SAXS)", Physics in Medicine and Biology, vol. 56, pp. 6779-6791. Oct. 5, 2011.
Miah et al. ("On-cloud healthcare clinic: an e-health consultancy approach for remote communities in a developing country." Telematics and Informatics 34.1 (2017): 311-322) (applying e-health solutions) (Year: 2017).
Office Action dated Apr. 21, 2026 for U.S. Appl. No. 18/056,219.
Office Action dated Apr. 23, 2026 for U.S. Appl. No. 18/827,350.
Miah et al. ("On-cloud healthcare clinic: an e-health consultancy approach for remotecountry." Telematics and Informatics 34.1 (2017): 311-322 (Year: 2017).
Notice of Allowance and Fees dated Dec. 2, 2025 for U.S. Appl. No. 18/352,094.
Notice of Allowance and Fees dated Oct. 21, 2025 for U.S. Appl. No. 18/298,228.
Office Action dated Nov. 26, 2025 for U.S. Appl. No. 18/500,616.
Office Action dated Oct. 30, 2025 for U.S. Appl. No. 18/352,085.
Office Action dated Oct. 9, 2025 for U.S. Appl. No. 18/298,218.
Choi Mina et al: "Feasibility of imaging amyloid in the brain using small-angle x-ray scattering", Biomedical Physics & Engineering Express, vol. 7, No. 1,Nov. 27, 2020 (Nov. 27, 2020), p. 015008, XP093329220, GB ISSN: 2057-1976, DOI: 10.1088/2057-1976/ab501c abstract section "2. Methods".
International Search Report and Written Opinion dated Nov. 7, 2025 for PCT Patent Application No. PCT/IB2025/056737.

* cited by examiner

FIG. 3A

DIAGNOSTIC SYSTEMS AND METHODS FOR ANIMAL PATIENTS WITH GLOBAL DATA CENTER AND LOCAL AUTONOMOUS CELL

BACKGROUND

Early diagnosis of severe pathological conditions, such as breast cancer, acute myocardial infarction, pericarditis and bradycardia of the heart, and ischemic and neurological strokes, is directly related to the successful treatment of a patient. There have been some efforts at the early detection and diagnosis of some types of diseases in humans and animals. Some have been "direct" methods to detect disease in human prostate, breast and brain tissue, and some have been "indirect" detection and diagnostic methods utilizing hair or nail samples to detect certain diseases.

Fiber diffraction patterns of skin or fingernails, using X-ray sources, have been used as a biometric diagnostic method for detecting neoplastic disorders such as melanoma, breast cancer, colon cancer and prostate cancer. It may be possible to conduct such tests at local radiology facilities (e.g., as a confirmatory test for other diagnostic procedures), or as a mass screening test using small angle X-ray beam-lines at synchrotron radiation facilities.

In another example, small-angle x-ray diffraction was used to study the structure of potential cancer sites in human prostate, breast and brain tissue. Diffraction patterns at small angles corresponded to large diffracting structures in the tissue material, and each tissue had a different and distinct diffraction pattern. Further, for a particular tissue, it was found that patterns from normal and pathological samples were different from each other.

SUMMARY

In some embodiments, the techniques described herein relate to a method for diagnosing diseases in animal patients including: providing a set of global data to a global data center; processing the set of global data and categorizing the processed set of global data into data clusters using a processor coupled to the global data center, wherein each data cluster corresponds to a diagnostic indicator for assessment of a physiological or pathological condition; measuring a local measurement data of a local patient using measurement equipment of a local autonomous cell, wherein the local patient is an animal; communicating the local measurement data and local patient data from the local autonomous cell to the global data center; processing the local measurement data and comparing the processed local measurement data with the data clusters to determine a local diagnostic indicator for the local patient using the processor; and communicating the local diagnostic indicator from the global data center to the local autonomous cell.

BRIEF DESCRIPTION OF THE DRAWINGS

FIG. 3A shows an example method for diagnosing diseases, in accordance with some embodiments.

DETAILED DESCRIPTION

Figure 1A:
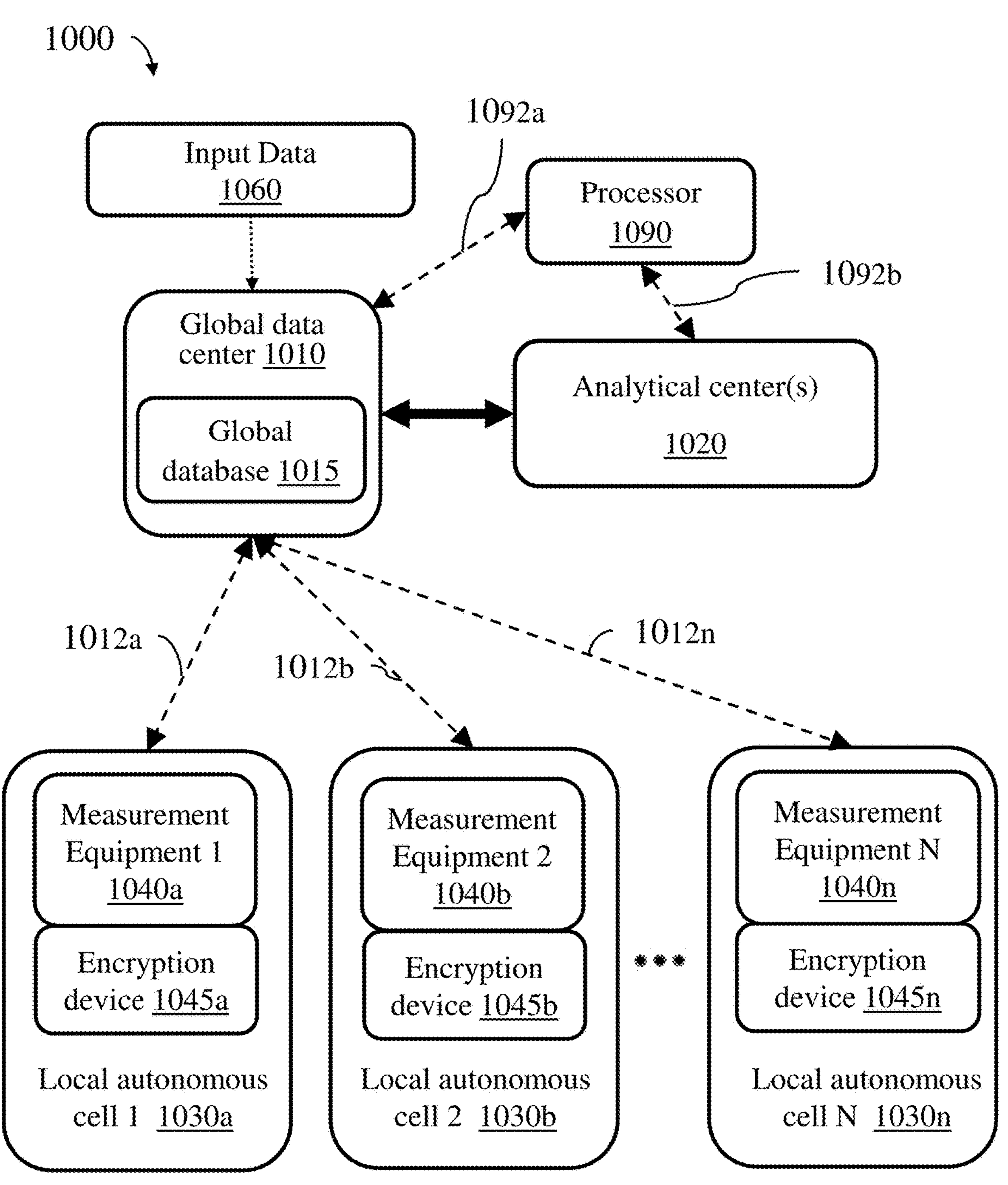
FIGS. 1A-1D show schematics of example systems for diagnosis of diseases, in accordance with some embodiments.

The present disclosure relates to diagnostic systems and methods for treating patients, for example, patients with one or more physiological or pathological conditions. The diagnostic systems and methods described herein include one or more local autonomous cells (LACs) containing measurement equipment configured to measure data from a local patient. The diagnostic systems and methods described herein also include a global data center (GDC) containing a set of global data categorized into data clusters. The data from the local patient can be provided to the GDC and processed, analyzed and compared with the data clusters to produce a diagnostic indicator related to the assessment of a physiological or pathological condition (e.g., cancer, or a cardiac condition).

The diagnostic systems and methods described herein include one or more LACs in communication with a GDC. The GDC is coupled to one or more processors for processing data. The processor(s) can be part of the GDC, or can be in the cloud and can and use cloud computing to process data (e.g., using a distributed network of computers). Optionally, the GDC can also be in communication with an analytical center (AC) containing the processor(s). The GDC has a set of global data, for example stored in a global database, from a set of global patients (i.e., a global set of animal patients), which can be from any location in the world, or from a specific geographical region or nation. The processor(s) (e.g., in the cloud, of the GDC, or of the AC) can process and categorize the set of global data into data clusters. In cases where the processor is part of the AC or is in the cloud, then the GDC can communicate the set of global data from the global database to the AC or to the processor in the cloud. Each data cluster can correspond to a diagnostic indicator for assessment of a physiological or pathological condition (e.g., cancer, or a cardiac condition). The LACs can also communicate one or more local measurement data of one or more local patients (where a local patient is one that is local to an LAC, e.g., a specific patient being treated/diagnosed by a veterinary services provider associated with the LAC) and local patient data (i.e., information about the local patient(s)) to the GDC. The GDC can then use its own processor, or provide the local measurement data to the processor of the AC or of the cloud, to process the local measurement data and compare the processed local measurement data with the data clusters to determine a local diagnostic indicator for each local patient. The local diagnostic indicator(s) can then be communicated, optionally from the AC to the GDC, and from the GDC to the LAC(s).

The diagnostic systems and methods described herein including the LAC(s) and the GDC (and optionally the AC)

are beneficial since they can enable early diagnosis of pathological conditions, such as breast cancer, acute myocardial infarction, pericarditis and bradycardia of the heart, and ischemic and neurological strokes. Early detection of such conditions or diseases is known to be directly related to the successful treatment of a patient. However, for the treatment of many diseases, there are no readily available, non-invasive and cost-effective diagnostic tests (especially for early detection), and diagnoses for patients often come too late for effective treatment. The diagnostic systems and methods described herein including the LAC(s) and the GDC (and optionally the AC) can beneficially provide reliable ways to diagnose serious diseases in animals and opportunities to expand the availability of diagnostic methods for animal patients.

The diagnostic systems and methods described herein including the LAC(s) and the GDC (and optionally the AC) can beneficially increase the accessibility of patients to diagnostic tools designed to assess one or more target physiological or pathological conditions of the patients. For example, the LACs of the diagnostic systems and methods described herein can measure the local measurement data of a local patient in a remote region (e.g., without internet connectivity), and then communicate with the GDC via mail to provide the analysis capabilities and access to the global data of the GDC to patients in the remote region.

The measurement equipment of the LACs in the diagnostic systems and methods described herein can include equipment for the direct measurement of tissue affected by a condition or disease, or an "indirect" detection of a tissue that shows an indicator that a different area of the body is affected by a disease. For example, samples of hair, nails, skin, wool, horns, hooves, and other biological animal samples, can be used to detect the presence of a condition or disease in a different part of the body (e.g., the molecular structure of a hair or nail sample measured using a tissue diffractometer can be used as an input for a diagnostic indicator related to the presence of cancer in a different part of the body).

The diagnostic systems and methods described herein can be designed to assess one or more target physiological or pathological conditions of a patient. The LACs of the diagnostic systems and methods described herein can comprise: a) one or more measurement equipment units intended for data collection for quantitative health indicator testing (e.g., designed for in vivo testing and/or for in vitro testing of a patient or a patient's tissue samples), b) a local database based on local memory devices designed to store patient data, measurement data (or testing results) and computer-aided diagnostic indicators intended for assessment of a physiological or pathological condition, and optionally c) a processor (or computer) designed to pre-process or process testing results and develop recommendations for the patient treatment based on the computer-aided diagnostic indicators. The GDC, the cloud, and/or the AC also contains a processor (or computer) designed to process the measurement data (or testing results) and to produce the computer-aided diagnostic indicators. The collected test results (local measurement data) are sent to the GDC, and the computer-aided diagnostic indicators are received from the GDC, using various known communication methods, such as air mail, courier mail, e-mail, or other electronic transfer methods (e.g., using a telecommunication system).

As used herein, the term "tissue diffractometer" generally refers to a diffractometer configured to record diffraction data from one or more tissue samples. The tissue diffractometer may be an X-ray diffractometer. In some instances, the tissue diffractometer may be configured to record diffraction data and image data.

The term "diagnostic indicator," or "computer-aided diagnostic indicator," as used herein, generally refers to an indicator comprising diagnostic information generated with the help of one or more computer processors. In some instances, the "diagnostic indicator" can include a probability score for the likelihood that a subject has a condition, such as arrhythmia and violation of the heart rate (tachycardia, parasystole). In some instances, the "diagnostic indicator" can include a diagnosis that a subject has a disease. Some examples of such a disease include one of more of breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of the heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extra-cerebral tumors, bacterial endocarditis (inflammation of the inner lining of the heart), and meningococcal meningitis (inflammation of the membranes of the brain and spinal cord), or any combination thereof.

As used herein, the terms "veterinary services provider" generally refer to a veterinarian practitioner or support staff. The "veterinary services provider" may be a veterinarian, a veterinary nurse, a dentist, a technician, a student, or the like. The "veterinary services provider" may be at least partially responsible for the health care of the animal patient.

As used herein, the term "animal" generally refers to a non-human living organism. Some examples of animals are non-human mammals such as dogs, cats, rats, mice, rabbits, guinea pigs, hamsters, and monkeys, and non-mammals such as birds, reptiles and amphibians. The term "animal" can refer to a domestic animal such as horses, ponies, cats, dogs, rabbits, mice, rats, hamsters, guinea pigs, squirrels, chinchillas and other animals.

As used herein, the term "patient" refers to an animal. The "patients" described herein can be animals that are using the diagnostic systems and methods described herein, for example, an animal that is being measured (or has tissue being measured) at an LAC.

In some cases, the diagnostic systems and methods described herein include measurement equipment that measure a tissue sample in vivo or in vitro. For in vitro measurements, the tissue samples that contain $\alpha$-keratin and/or collagen, for example, hair, nails, skin, wool, horns, hooves, and/or biological samples of internal organs of an animal obtained as a result of biopsy. In some cases, the tissue sample can include one or more of: a surgical sample, a resection sample, a pathology sample, a biopsy sample, or any combination thereof. Such procedures can be performed at an LAC or at another facility that is not part of an LAC. In some cases, the tissue sample can be provided to the LAC by the patient or by a veterinary services provider of the patient. In some cases, patient data can accompany the tissue sample, and the patient data can include one or more of genetic data, or pathology lab data, or descriptions or data related to symptoms of the local patient. For example, patient data can include descriptions or data related to symptoms such as one or more of sleep disorders, insomnia, sudden awakenings, somnambulism, apnea, disorders of cerebral circulation, electroencephalogram (EEG) data, sudden convulsions and fainting, headaches and dizziness, and traumatic brain injuries and symptoms thereof.

In some cases, the diagnostic systems and methods described herein include a local database associated with an LAC. Such a local database can be stored on an electronic storage unit coupled to a processor of the LAC. Electronic storage units are discussed further herein and can include random access memory (RAM), cache memory, permanent storage device (ROM), hard disks, floppy disks, flash cards, streamers, and/or optical disks (CD or DVD). The local database can store local measurement data as well as symptoms of physiological or pathological conditions of local patients, such as sleep disorders including insomnia, sudden awakenings, somnambulism, apnea, disorders of cerebral circulation, EEG after strokes and micro-strokes, sudden convulsions and fainting, headaches and dizziness, and/or traumatic brain injuries and their consequences.

In some cases, the diagnostic systems and methods described herein include one or more method blocks wherein local measure data (or test results) and computer-aided diagnostic indicators are communicated between one or more LACs and a GDC at intervals of time that are either irregular or regular, approximately once a day, approximately once a week, or approximately once a month, or at shorter (e.g., continuous monitoring) or longer (e.g., yearly) interval lengths.

In some cases, the diagnostic systems and methods described herein include measurement equipment such as one or more electrocardiographs (ECGs), equipment for daily (Holter) monitoring, echocardiographs, electroencephalographs, magnetic resonance imaging (MRI) machines, computerized tomography (CT) machines, equipment for blood analysis, equipment for urine analysis, liquid chromatography-mass spectroscopy equipment (e.g., to measure metabolites, for example, in blood, urine, or tissue), tissue diffractometers configured to perform small angle X-ray scattering (SAXS) measurements, and/or tissue diffractometers configured to perform wide angle X-ray scattering (WAXS) measurements. Additionally, the diagnostic systems and methods described herein include spectroscopy measurement equipment such as atomic absorption spectroscopy (AAS), inductively coupled plasma optical emission spectroscopy (ICP-OES), and inductively coupled plasma mass spectrometry (ICP-MS), for example, to measure trace metals (e.g., in blood, urine, or tissue samples).

In some cases, the diagnostic systems and methods described herein include a user interface that allows an individual patient's owner, or a veterinary services provider (or healthcare provider) of the patient to send (e.g., by mail) the tissue sample. In another embodiment, the user interface is further configured to allow an individual patient's owner, or a veterinary services provider (or healthcare provider) of the patient, to make payments or upload an individual patient's signed consent form.

The LAC(s) of the diagnostic systems and methods described herein can communicate with the GDC using any methods, such as mail, airmail, courier mail, e-mail, or by transferring data electronically (e.g., over a telecommunications network). This enables LACs from any location to take measurement data of a local patient and then get a diagnostic indicator from the GDC (and optionally the AC), which can benefit the local patient and veterinary service providers of the local patient. This can be advantageous, for example, because one or more of the LACs does not need to have an internet connection for the method to be carried out. For example, one or more LACs can be located in remote regions, developing regions, or regions after disasters, and the LACs can communicate with the GDC using any available means. The communication of information between the GDC and the AC, when included, can be done electronically (e.g., over a telecommunications network).

In some embodiments, the LACs include a plurality of measurement equipment operably coupled to a computer database over a network, where the plurality of measurement equipment is configured to record and to assess one or more target physiological or pathological conditions of subject. The measurement equipment can include equipment intended for data collection for quantitative health indicators of a patient. The measurement equipment can include equipment designed for in vivo testing of patients or in vitro testing of tissue samples. For example, the measurement equipment can be an X-ray diffractometer configured to measure a structural property of a tissue sample. In another example, the measurement equipment can be an electrocardiograph machine, measuring and recording the electric fields appearing during the operation of the heart muscle of a local patient. The measured local measurement data and local patient data can be saved to a local or cloud-based computer database. The term "cloud," as used herein, refers to shared or sharable storage of electronic data, e.g., a distributed network of computer servers. In some instances, the cloud may be used for archiving electronic data, sharing electronic data, and/or analyzing electronic data. The LAC(s) can also include one or more computers to control the measurement equipment of the LAC(s). The LAC(s) can also include electronic data storage devices (e.g., coupled to a computer controlling measurement equipment) to locally store local measurement data and local patient data, or the LAC(s) can use cloud-based electronic data storage, e.g., that resides on one more remote computer servers.

The measurement equipment of the LACs can include one or more of an ECG machine, equipment for daily (Holter) monitoring, an echocardiograph machine, an MRI machine, a CT machine, equipment for blood analysis, equipment for urine analysis, liquid chromatography-mass spectroscopy equipment (e.g., to measure metabolites, for example, in blood, urine, or tissue), a tissue diffractometer configured to perform SAXS measurements, a tissue diffractometer configured to perform WAXS measurements, an electroencephalograph machine, and spectroscopy measurement equipment such as atomic absorption spectroscopy (AAS), inductively coupled plasma optical emission spectroscopy (ICP-OES), and inductively coupled plasma mass spectrometry (ICP-MS), for example, to measure trace metals (e.g., in blood, urine, or tissue samples). In some cases, the systems or methods described herein include more than one LAC in communication with the GDC. In such cases, each LAC can have one or more of the same type or different types of the aforementioned measurement equipment, and different LACs in the same system or method can include of the same type or different types of the aforementioned measurement equipment. For example, a system or method described herein can include 20 LACs, wherein 10 of the LACs include tissue diffractometers and 10 of the LACs include spectroscopy equipment. In another example, a system or method described herein can include eight LACs, wherein seven of the LACs include ECG machines and echocardiograph machines, and one of the LACs includes MRI and CT machines.

The global data center (GDC) and the analytical center (AC) of the diagnostic systems and methods described herein can communicate electronically, for example, through a telecommunications network (e.g., the Internet, an internet and/or extranet, or an intranet and/or extranet that is in communication with the Internet). The global database of the GDC can be a cloud-based database, e.g., a database that resides on one more remote computer servers. In some instances, the global database may be stored on a computer database residing on a computer of the GDC. The global database can contain measurement data measured by measurement equipment of the systems described herein and/or the global database can contain measurement data from measurement equipment that is outside of the systems described herein.

The processor of the GDC, the cloud, and/or the AC can be configured to process local measurement data (e.g., from the LAC(s)) and/or other data pertinent to the patient using a data analytics algorithm to provide a computer-aided diagnostic indicator for one or more local patients. The data analytics algorithm can be updated randomly, periodically, or continually, and can be refined using data from a set of global data from a set of global patients stored in the global database of the GDC. In some instances, the computer-aided diagnostic indicator can include an indicator of the likelihood that the patient has a disease, such as those described herein. In some instances, the computer-aided diagnostic indicator may include a diagnosis that the patient has a disease, such as those described herein. In some cases, the processor of the GDC, the cloud, and/or the AC can be distributed across more than one physical location, for example, the GDC and/or the AC can contain computers in more than one facility, or can use cloud computing to process data using a distributed network of computers.

In some embodiments, the GDC and the AC are collocated (e.g., in the same building, or in the same local area network). In such cases, the GDC and the AC can both utilize the same one or more computer processors.

In some cases, the local measurement data can be sent from measurement equipment to the LAC(s) in real-time or in substantially real-time. This can be the case when the measurement equipment is located in the LAC, and can also be the case when measurement equipment of an LAC is not located within the LAC. For example, the measurement equipment could be a wearable electrocardiograph machine that can be worn by a patient throughout the day and can be associated with an LAC but be in a different physical location than the LAC, and can communicate with a computer of the LAC in real-time, or in substantially real-time.

In some cases, local measurement data can be sent from an LAC to the GDC in real-time or substantially real-time, for example by transferring data electronically (e.g., over a telecommunications network). In some instances, a stream of local measurement data can be transmitted from the LAC(s) the GDC. In some instances, the local measurement data can be transmitted from an LAC to the GDC in packets (e.g., bundles of one or more pieces of local measurement data) in near-real time. For example, a series of local measurement data of a plurality of patients can be taken throughout a day and can then be all transmitted from the LAC to the GDC together. In another example, all local measurement data taken of a single subject during a single scan or single session can be transmitted from the LAC to the GDC together. The transmitting from the LAC to the GDC can be real-time transmitting, substantially real-time transmitting, intermittent transmitting (e.g., transmitting packets), or any combination thereof.

In some embodiments, the diagnostic systems and methods described herein further comprise a user interface (UI) through which a local patient's owner or a veterinary services provider can interact with the system. The UI can be viewed on a computer screen, or on a tablet, and can be interacted with using a touch screen or an input device, for example. The user interface may be configured to allow the local patient's owner and/or their veterinary services provider to upload the local measurement data and/or the local patient data to the system. For example, the UI can be used to upload a local measurement data (e.g., numerical data for example in a spreadsheet, an electronic image, or a scanned version of a hard copy of an image) to a computer of an LAC, or in some cases, directly to the GDC (e.g., for processing by the GDC or the AC, and/or for storage in the global database). In some cases, the local measurement data and/or the local patient data can be uploaded through the UI, the local measurement data and/or the local patient data can be sent to the GDC, processed by the GDC or the AC, and the diagnostic indicator produced can then be communicated to the local patient's owner and/or their veterinary service provider through the UI. In other cases, the local measurement data and/or the local patient data can be uploaded through the UI and a diagnostic indicator can be received through the UI, without the local measurement data and/or the local patient data being sent to the LAC or to the GDC. In such cases, the local measurement data and/or the local patient data can be processed by the AC, and the diagnostic indicator produced by the AC can be provided to the UI for communication to the local patient's owner and/or their veterinary service provider. The role of the GDC in such an example would be to provide the set of global data to the AC for the categorization into data clusters.

In some cases, the uploading of the local measurement data and/or the local patient data may be done in exchange for processing the individual patient's data, local measurement data, or any combination thereof to receive the computer-aided diagnostic indicator for the individual patient for (e.g., without cost to the local patient). The UI can be configured to allow a local patient's owner and/or their veterinary services provider to make payments and/or upload an individual consent form signed by the local patient. The payments can be cash payments (e.g., the user interface displays an address to send the payments), check payments (e.g., paper or electronic check payments), card payments (e.g., credit or debit card payment processing), app-based payments (e.g., PayPal®, Venmo®), cryptocurrency payments (e.g., Bitcoin), or any combination thereof. The individual consent form may be signed by the local patient's owner and/or the veterinary services provider. The individual consent form may be related to the computer-aided diagnostic indicator. For example, the local patient's owner can sign and upload an individual consent form stating that the local measurement data of the local patient can be retained on the global database of the GDC. In some instances, the individual consent form may be physically signed, electronically signed, or any combination thereof.

The diagnostic systems and methods described herein can contain two or more LACs, each in communication with the GDC, and the GDC (and optionally the AC) can serve as central storage and/or processing facilities. For example, the systems and methods described herein can include 1, 2, 3, 4, 5, 6, 7, 8, 9, 10, 20, 30, 40, 50, 60, 70, 80, 90, 100, 150, 200, 250, 300, 350, 400, 450, 500, more than 500, or from 1 to more than 500, local autonomous cells which each comprise measurement equipment, each operatively coupled to a local computer. Since each LAC can contain measurement equipment, the systems and methods described herein can likewise include 1, 2, 3, 4, 5, 6, 7, 8, 9, 10, 20, 30, 40, 50, 60, 70, 80, 90, 100, 150, 200, 250, 300, 350, 400, 450, 500, more than 500, or from 1 to more than 500 measurement equipment units.

The GDC can contain a global database in which the set of global data is stored. The global data can include measurement data from patients, and additional information related to the patients and/or related to diagnostic indicators associated with data clusters. The LACs and AC can also be coupled to electronic storage devices (i.e., that is local to the AC) and/or be in communication with electronic storage devices in the cloud. The global database can also reside on a central computer server, on an electronic storage device coupled to a computer of the GDC, and/or on an electronic storage device in the cloud. In some instances, the central computer server can be a cloud-based computer server comprising a distributed network of remote computer servers. In some instances, the computer database may reside on a server that is coupled to a computer of the GDC (i.e., that is local to the GDC). In some instances, data (e.g., local measurement data, or a set of data from the global database) may be transferred or exchanged between a local computer database (i.e., a computer database that is local to the LAC, GDC or AC) and a remote or central computer database (i.e., a computer database that is in the cloud, or on a distributed network of computers). In some cases, the data stored by the LAC(s), GDC and/or AC, can reside on a privacy law compliant server (e.g., a HIPAA compliant server).

In some instances, the data analytics algorithm used by the processor of the GDC, the cloud, or the AC to process local measurement data and provide a computer-aided diagnostic indicator can include the use of one or more statistical algorithms. For example, points and features can be extracted from a set of global data (e.g., using analytical methods, numerical methods, machine learning methods, etc.), and statistical algorithms can be used to categorize the data into the data clusters using the calculated metrics. Statistical algorithms can also be used when comparing local measurement data with the data clusters to determine a local diagnostic indicator for the local patient. For example, the metrics of local measurement data can be compared with the data clusters to determine which data cluster the local measurement data is most closely associated. The diagnostic indicator for the local patient can then be determined to be the one that is associated with the closest data cluster. In some cases, a cluster center of each data cluster can be determined using statistical analyses, and the metrics of the local measurement data of a local patient (and in some cases the patient data) can be translated into a local data point which can be compared with the cluster centers. For example, the data cluster associated with local measurement data can be the one that has the shortest distance between the local data point and the cluster center of that data cluster.

In some instances, the data analytics algorithm used by the processor of the GDC, the cloud, or the AC to process local measurement data and provide a computer-aided diagnostic indicator can include the use of one or more machine learning algorithms. The one or more machine learning algorithms may be configured to operate upon local measurement data, local patient data, global data from the global database, patient data from the global database, or any combination thereof. The machine learning algorithm can include one or more supervised learning algorithms, one or more unsupervised learning algorithms, one or more semi-supervised learning algorithms, one or more reinforcement learning algorithms, one or more deep learning algorithms, or any combination thereof. The machine learning algorithm may be a deep learning algorithm. The deep learning algorithm can include one or more convolutional neural networks, one or more recurrent neural networks, and/or one or more recurrent convolutional neural networks.

In some embodiments of the diagnostic systems and methods described herein, statistical analysis algorithms and/or machine learning algorithms can be implemented on a local computer (i.e., one that is local to an LAC, the GDC or the AC), or a remote server (e.g., one that is in the cloud, or in a distributed network of computers). For example, a machine learning algorithm can be configured to preprocess raw local measurement data, and/or patient data to remove noise or other artifacts. A different machine learning algorithm can be trained to identify features within the local measurement data, and/or patient data. Such a machine learning algorithm can cluster data points for use as an identification algorithm. Other machine learning algorithms can be configured to provide a computer-aided diagnostic indicator.

The machine learning algorithms used by the diagnostic systems and methods described herein may include a supervised, semi-supervised, or unsupervised machine learning algorithm. A supervised machine learning algorithm, for example, is an algorithm that is trained using labeled training data sets, e.g., data sets that comprise training inputs with known outputs. The training inputs can be provided to an untrained or partially trained version of the machine learning algorithm to generate a predicted output. The predicted output can be compared to the known output in an iterative process, and if there is a difference, the parameters of the machine learning algorithm can be updated. A semi-supervised machine learning algorithm is trained using a large set of unlabeled training data, e.g., unlabeled training inputs, and a small number of labeled training inputs. An unsupervised machine learning algorithm, e.g., a clustering algorithm, may find previously unknown patterns in data sets comprising data with no pre-existing labels.

For example, a machine learning algorithm that can be used to perform some of the functions described above (e.g., processing of global data, local measurement data, patient data, and/or generating computer-aided diagnostic indicators) is a neural network. Neural networks employ multiple layers of operations to predict one or more outputs, for example, a likelihood that a subject has a disease, from one or more inputs, for example, measurement data, patient data, processed data derived from measurement data, and/or patient data, or any combination thereof. Neural networks can include one or more hidden layers situated between an input layer and an output layer. The output of each layer can be used as input to another layer (e.g., the next hidden layer or the output layer). Each layer of a neural network can specify one or more transformation operations to be performed on the data input to the layer. Such transformation operations may be referred to as "neurons." The output of a particular neuron may be, for example, a weighted sum of the inputs to the neuron, that is optionally adjusted with a bias and/or multiplied by an activation function (e.g., a rectified linear unit (ReLU) or a sigmoid function).

Training a neural network that can be used to perform some of the functions described above (e.g., processing of global data, local measurement data, patient data, and/or generating computer-aided diagnostic indicators) can involve providing inputs to the untrained neural network to generate predicted outputs, comparing the predicted outputs to expected outputs, and updating weights and biases of the algorithm in an iterative manner to account for the difference between the predicted outputs and the expected outputs. For example, a cost function can be used to calculate a difference between the predicted outputs and the expected outputs. By computing the derivative of the cost function with respect to the weights and biases of the network, the weights and biases can be iteratively adjusted over multiple cycles to minimize the cost function. Training may be complete when the predicted outputs satisfy a convergence condition, such as obtaining a small magnitude of calculated cost.

Convolutional neural networks (CNNs) and recurrent neural networks can be used to process, analyze, classify, or make predictions from global data, local measurement data, patient data, or any combination thereof. CNNs are neural networks in which neurons in some layers, called convolutional layers, receive data from only small portions of a data set. These small portions may be referred to as the receptive fields of the neurons. Each neuron in such a convolutional layer may have the same weights. In this way, the convolutional layer can detect features, e.g., diagnose changes in myocardium, in any portion of the input measurement data.

RNNs, meanwhile, are neural networks with cyclical connections that can encode dependencies in time-series data, and can be used to perform some of the functions described herein, for example, those related to local measurement data collected over time, and longitudinal studies of one or more patients. An RNN may include an input layer that is configured to receive a sequence of time-series inputs, e.g., local measurement data, patient data, or any combination thereof collected over a period of time. An RNN may also include one or more hidden recurrent layers that maintain a state. At each time step, each hidden recurrent layer can compute an output and a next state for the layer. The next state can depend on the previous state and the current input. The state can be maintained across time steps and can capture dependencies in the input sequence. In some cases, such an RNN can be used to determine time-series features or evolutions of features within local measurement data and/or patient data.

An example of an RNN that can be used to perform some of the functions described herein is a long short-term memory network (LSTM), which can be made of LSTM units. An LSTM unit can be made of a cell, an input gate, an output gate, and a forget gate. The cell can be responsible for keeping track of the dependencies between the elements in the input sequence. The input gate can control the extent to which a new value flows into the cell, the forget gate can control the extent to which a value remains in the cell, and the output gate can control the extent to which the value in the cell is used to compute the output activation of the LSTM unit. The activation function of the LSTM gate may be, for example, the logistic function.

Other examples of machine learning algorithms that can be used to perform some of the functions described herein (e.g., to process and categorize global data, local measurement data, patient data, or any combination thereof) are regression algorithms, decision trees, support vector machines, Bayesian networks, clustering algorithms, reinforcement learning algorithms, and the like.

For example, a clustering algorithm can be used, which can be a hierarchical clustering algorithm in some cases. A hierarchical clustering algorithm can be a clustering algorithm that clusters patients based on their proximity to other patients. For example, a hierarchical clustering algorithm can cluster global data, local measurement data, patient data, or any combination thereof. The clustering algorithm can alternatively be a centroid-based clustering algorithm, for example, a k-means clustering algorithm. A k-means clustering algorithm can partition a set of (n) observations into a set of (k) data clusters, where each observation belongs to the data cluster with the nearest mean. The mean can serve as a prototype for the data cluster. In the context of global data, local measurement data, patient data, or any combination thereof, a k-means clustering algorithm can generate distinct groups of data that are correlated with each other. Thereafter, each group of data can be associated with a particular data cluster, based on knowledge about that subsystem (e.g., knowledge about previous diagnoses and data). As described herein, each data cluster can be associated with a diagnostic indicator, which can be, for example, a probability or diagnosis of a condition (e.g., of a disease described herein). The clustering algorithm can alternatively be a distribution-based clustering algorithm, for example, a Gaussian mixture model or expectation maximization algorithm. Examples of other clustering algorithms are cosine similarity algorithms, topological data analysis algorithms, and hierarchical density-based clustering of applications with noise (HDB-SCAN).

The machine learning algorithms that can be used to perform some of the functions described herein (e.g., to process and categorize global data, local measurement data, patient data, or any combination thereof) can be trained using a training dataset comprising global data, local measurement data, patient data, or any combination thereof. The training dataset may be stored in a computer database of the system (e.g., the global database) for a specific pathology and/or physiological norm group. The training dataset may be obtained using local measurement data provided to the GDC by the LAC(s), or the training dataset can include global data, local measurement data, and/or patient data from any source (e.g., a government-operated database). The training dataset can include information regarding a confirmation of a diagnosis for a given set of data. For example, such information can include a plurality of images and ECGs suspected of changes in myocardium, thinning, or thickening of the heart muscle, and/or an ultrasound examination of the carotid arteries for the presence of atherosclerosis. A set of ECGs can be accompanied by information regarding the longevity of the subject that the ECGs were taken from. The computer database of the systems and methods described herein for a specific pathology and/or physiological norm group may be a remote computer database (e.g., a cloud-based database) or a local database (e.g., a computer system local to an LAC, GDC or AC). For example, the training dataset for coronary heart disease diagnostic indicators can be stored on a computer database of the system with other coronary heart disease diagnostic data.

The training dataset may be updated as new global data, local measurement data, patient data, or any combination thereof is uploaded to the global database. The updating may be an inclusion of the new data, a removal of the old data, or a combination thereof. For example, new patient data can be added to the training dataset as it is taken (e.g., in real-time, or substantially real-time) or after it is taken to improve the quality of the training dataset. In another example, poor quality data may be removed from the training dataset when higher quality new data is added. The statistical analysis algorithm and/or machine learning algorithm (e.g., the data analytics algorithm) used by the systems and methods described herein may be updated when the computer database or training dataset residing thereon is updated. For example, a machine learning algorithm can be retrained using the new training dataset to improve the efficacy of the machine learning algorithm in generating a computer-aided diagnostic indicator. The statistical analysis and/or machine learning algorithm may be continuously, periodically, or randomly updated and refined as the training dataset is updated. In this example, the revised statistical analysis and/or machine learning algorithm may be more accurate, specific, and/or sensitive in providing a probability or diagnosis than a previous version derived from a previous training dataset.

The diagnostic systems and methods described herein are configured to communicate a computer-aided diagnostic indicator to a local patient. The computer-aided diagnostic indicators can include an indicator of a likelihood that the local patient has a disease, such as cancer, heart disease, or other disease described herein. For example, a computer-aided diagnostic indicator can include a banded risk assessment for the local patient (e.g., high risk, medium risk, low risk). The computer-aided diagnostic indicator may be displayed on a UI, as described herein. The computer-aided diagnostic indicator may be a report in some cases. The report may be a printed report, and it can include additional information. For example, the report can include a likelihood of the patient having a chronic lung disease, as well as the indicators that contributed to the generation of the report and a suggestion of possible next steps for the patient to take. The indicator may be a percentage (e.g., a percentage likelihood that the patient has the disease), a risk band (e.g., high risk, medium risk, low risk), comparison of factors (e.g., a list of factors indicating a presence and a list of factors indicating an absence), or the like, or any combination thereof. For example, a diagnostic indicator can contain an indicator of the likelihood that the individual patient has a disease (e.g., chronic lung disease), which may be an indicator of the likelihood that the individual patient has another condition or disease (e.g., thromboembolism).

In some cases, a diagnostic indicator may contain a diagnosis that the local patient has a disease, such as those described herein. A computer-aided diagnostic indicator for an individual patient may contain a diagnosis that an individual patient has a disease. A diagnostic indicator can be generated, at least partially, using a statistical analysis algorithm and/or a machine learning algorithm. A diagnostic indicator can be generated, at least in part, using the input data of a healthcare provider. For example, a health care provider may be presented with a list of indicators and risk ranges, and the health care provider may make a final decision regarding the patient's diagnosis. In such cases, the global database used to establish the data clusters can also be provided to the GDC by the health care provider. In some cases, a diagnostic indicator of the diagnostic systems and methods described herein may have accuracy, selectivity and/or specificity of at least about 10%, 20%, 30%, 40%, 50%, 60%, 70%, 80%, 90%, 95%, 98%, 99%, 99.9%, or even more. In some cases, the diagnostic indicator may have accuracy, selectivity and/or specificity of no more than 99.9%, 99%, 98%, 95%, 90%, 80%, 70%, 60%, 50%, 40%, 30%, 20%, 10%, or less. Any of the lower and upper values described in this paragraph can be combined to form the range of the accuracy, selectivity and/or specificity of the diagnostic indicator, for example, in some cases, a diagnostic indicator may have accuracy, selectivity and/or specificity that ranges from about 80% to about 99%. A diagnostic indicator may have accuracy, selectivity and/or specificity that has any value in this range, for example, about 98.6%.

FIG. 1A shows a schematic of an example system 1000 for diagnosis of diseases (e.g., cancer, heart disease, lung disease, or any of the diseases described herein), in accordance with some embodiments. System 1000 includes global data center (GDC) 1010, analytical center (AC) 1020, and local autonomous cells (LACs) 1030*a*, 1030*b* and 1030*n*. GDC 1010 includes a global database 1015 residing on a local storage device, a central server, or in the cloud, wherein a set of input data 1060 is stored. Each of the LACs 1030*a*, 1030*b* and 1030*n* has a respective measurement equipment 1040*a*, 1040*b* and 1040*n*. The measurement equipment 1040*a*, 1040*b* and 1040*n* can include equipment intended for data collection for quantitative health indicators of patients. The measurement equipment 1040*a*, 1040*b* and 1040*n* can include equipment designed for in vivo testing of patients or in vitro testing of tissue samples of the patient. The GDC 1010 and/or the AC 1020 can include a processor (not shown) for processing data.

GDC 1010 and AC 1020 are in communication with one another such that information (e.g., global data, local measurement data, patient data, or diagnostic indicators) can be electronically transferred between GDC 1010 and AC 1020. For example, GDC 1010 and AC 1020 can communicate through a network (e.g., the Internet, an internet and/or extranet, or an intranet and/or extranet that is in communication with the Internet).

GDC 1010 is also in communication with each of the LACs 1030*a*, 1030*b* and 1030*n* through respective communication channels 1012*a*, 1012*b* and 1012*n*, which can operate by any means. For example, communication channels 1012*a*, 1012*b* and 1012*n* can use mail, airmail, courier mail, e-mail, and/or electronic information transfer means (e.g., one or more networks) to transfer data and information between the GDC 1010 and each of the LACs 1030*a*, 1030*b* and 1030*n*. For example, local measurement data of a local patient can be saved to a digital storage medium (e.g., a flash drive) by the LAC, and sent from the LAC to the GDC by mail, airmail or courier mail over communication channels 1012*a*, 1012*b* and 1012*n*. In another example, local measurement data of one or more local patient(s) can be printed to hard copies (e.g., graphs and/or numerical information can be printed on paper), the hard copies of the local measurement data can be sent to the GDC by mail, airmail or courier mail over communication channels 1012*a*, 1012*b* and 1012*n*, and the GDC or the AC can digitize the hard copies of the local measurement data so that it can be processed by the AC. In other cases, communication channels 1012*a*, 1012*b* and 1012*n* are configured to communicate data and information electronically, for example, using a telecommunication system.

In some cases, GDC 1010 and/or the AC 1020 can be coupled to a processor 1090 in the cloud (i.e., processor 1090 can be located remotely from the GDC 1010 and from AC 1020, and, for example, be configured to perform cloud computing or to process data from the GDC 1010 and/or from the AC 1020, for example, using a distributed network of computers) using respective communication channels 1092*a* and 1092*b*. Communication channels 1092*a* and 1092*b* can be configured such that data can be sent electronically between the GDC 1010 or from the AC 1020 to the processor 1090 (e.g., using a telecommunications system). In some cases, as described further herein, the system does not include the AC 1020, and the GDC is coupled to the processor 1090 in the cloud, which processes data from the GDC 1010 without using the AC 1020.

In some embodiments of system 1000, local measurement data and local patient data of a local patient is communicated from one of the LACs 1030*a*, 1030*b* and 1030*n* to GDC 1010. The local patient data is associated with the local measurement data of the local patient. The local patient data can include, for example, descriptions or data related to symptoms of the local patient comprising one or more of: sleep disorders, insomnia, sudden awakenings, somnambulism, apnea, disorders of cerebral circulation, electroencephalogram (EEG) data, sudden convulsions and fainting, headaches and dizziness, and traumatic brain injuries and symptoms thereof. The local patient data can also include, for example, one or more of: age, gender, profession, blood pressure, body weight, body-mass index (BMI), cholesterol, cooccurrence of neurological diseases, registration in a cardio-dispensary, patient ethnicity, genetic data, and behavioral data, symptoms, reports from the patient, reports of discomfort, reports of chest pain, reports of back pain, reports of shortness of breath, leg swelling, information about chest injury, information about sustained hypertension, reports of constant and severe upper abdominal pain, and any other information related to the local patient.

Global database 1015 can contain a set of global data. The input data 1060 can be data that is added to the global data of global database 1015. In some cases, the local measurement data of the local patient can also be added to the global database 1015. In some cases, in future instances, the local measurement data can be included in the set of global data that is processed and categorized into data clusters by the processor of the GDC, cloud, or AC.

In system 1000, the measurement equipment 1040*a*, 1040*b* and 1040*n* of the respective LACs 1030*a*, 1030*b* and 1030*n*, are configured to measure local measurement data of local patients. The local measurement data of a local patient is likewise measured using one of the measurement equipment 1040*a*, 1040*b* and 1040*n*.

In some embodiments, the measurement equipment 1040*a*, 1040*b* and 1040*n* can each be a tissue diffractometer configured to measure molecular structure of biological tissue of a patient, either in vivo or in vitro. Methods and systems of using tissue diffractometers measure biological tissue of a patient and to produce a diagnostic indicator are described in U.S. Pat. Nos. 11,607,188 and 11,751,828, and in U.S. patent application Ser. Nos. 18/352,085 and 18/352,094, the contents of which are incorporated by reference.

In some embodiments, the LAC(s) 1030*a*, 1030*b* and 1030*n* and/or the measurement equipment 1040*a*, 1040*b* and 1040*n* are mobile and/or portable. For example, each LAC (s) 1030*a*, 1030*b* and/or 1030*n* can be configured in a vehicle, such that they are mobile. In other examples, the LAC(s) 1030*a*, 1030*b* and 1030*n* are stationary (e.g., located in a building) and the measurement equipment 1040*a*, 1040*b* and 1040*n* is portable. In such cases, the measurement equipment 1040*a*, 1040*b* and 1040*n* can be in communication with an associated LAC, as described further herein. Some examples of measurement equipment 1040*a*, 1040*b* and 1040*n* that can be portable are ECG machines, or equipment for collecting blood, urine or tissue samples.

In system 1000, the AC 1020 has a processor configured to process global data and categorize them into data clusters, wherein each data cluster corresponds to a diagnostic indicator for assessment of a physiological or pathological condition. For example, the set of input data 1060 (or all global data in the global database 1015) can be processed by the processor of the AC 1020 to categorize them into data clusters. Then, a local measurement data of a local patient can be processed by the processor of the AC 1020, and the processed local measurement data can be compared with the data clusters (from the global data, or from the set of input data 1060) to determine a local diagnostic indicator for the local patient. For example, the processor can process the set of global data and categorize the processed set of global data into data clusters by performing a statistical analysis on the processed set of global data.

Each of the data clusters can correspond to a diagnostic indicator for assessment of a physiological or pathological condition. For example, the diagnostic indicators can relate to one of more of: breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of the heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extra-cerebral tumors, bacterial endocarditis (inflammation of the inner lining of the heart), and meningococcal meningitis (inflammation of the membranes of the brain and spinal cord). In the case of heart-related conditions and diseases, the diagnostic indicators can relate to one of more of: the detection of arrhythmia and heart rate violation, the detection of tachycardia, the detection of parasystole, diagnosing failures in conducting nerve impulses inside the heart, identification of acute and chronic changes, identification of myocardial infarction, identification of coronary heart disease, identification of acute and chronic lung diseases, identification of thromboembolism, identification of chronic bronchitis, diagnosis of changes in myocardium, diagnosis of heart muscle thinning, diagnosis of thickening of the heart muscle, diagnosis of myocarditis, and diagnosis of inflammation of the heart muscle.

In some embodiments of system 1000, the processor of the AC 1020 processes and categorizes the global data, input data 1060, or local measurement data using a machine learning algorithm. For example, the machine learning algorithm can include a supervised learning algorithm, an unsupervised learning algorithm, a semi-supervised learning algorithm, a reinforcement learning algorithm, a deep learning algorithm, or any combination thereof. The machine learning algorithm can also include a convolutional neural network, a recurrent neural network, or a recurrent convolutional neural network. In some cases, the machine learning algorithm can be trained using a training dataset comprising training measurement data, training patient data, or any combination thereof, wherein the training dataset comprises data from a set of training patients with known pathologies or physiological norm groups. In such cases, the training dataset can be updated with new training measurement data, new training patient data, or any combination thereof, upon the new training measurement data being added to the global data center.

In some cases, the LACs 1030*a*, 1030*b* and 1030*n* of system 1000 can be in different geographic locations. For example, each LAC can be in a different geographic location, or two or more LACs can be in one location and other LACs can be in different geographic locations. In some cases, different geographic locations can include different buildings, different neighborhoods, different cities, different states, or different countries.

Figure 1B:
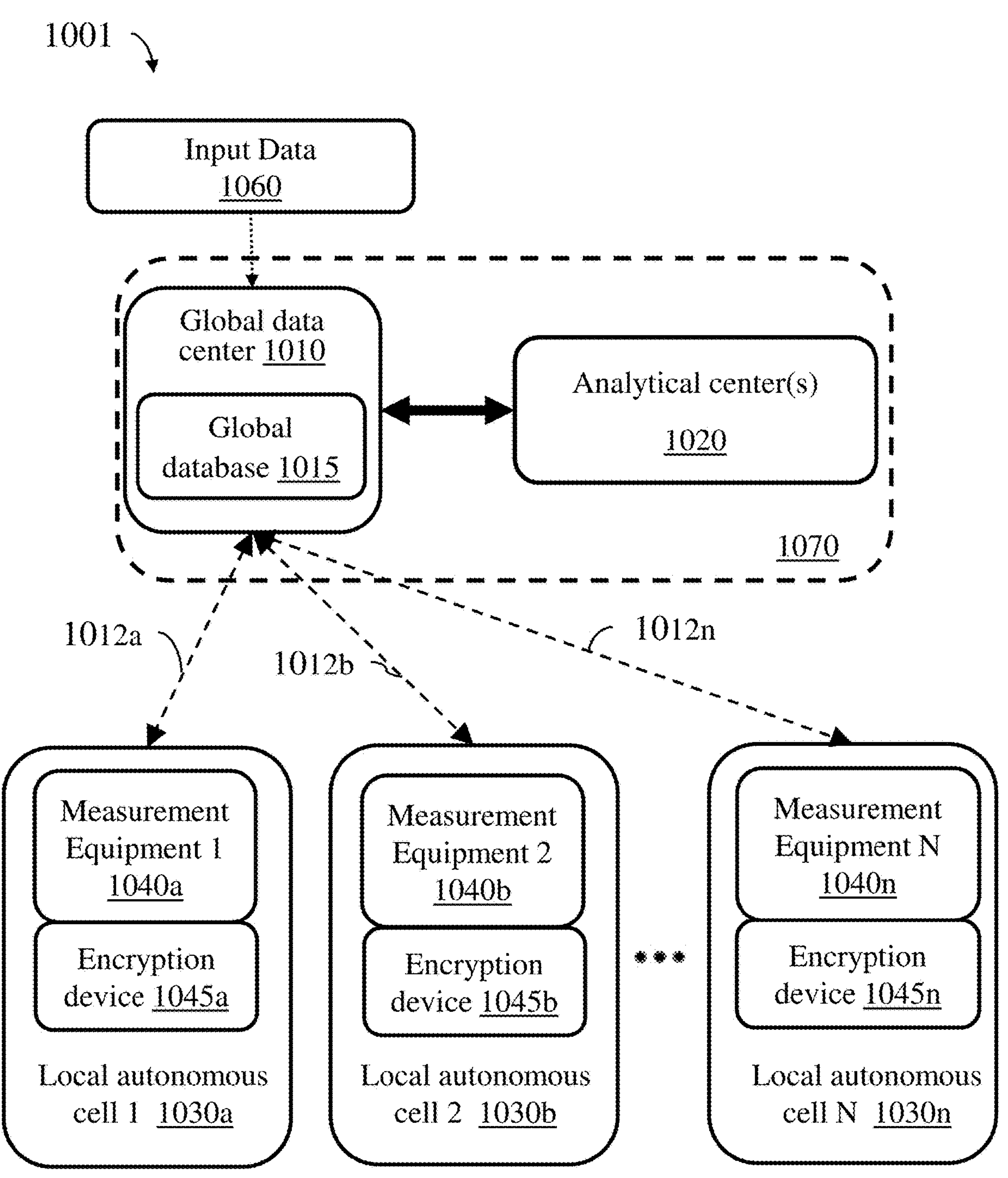

FIG. 1B shows a schematic of an example system 1001 for diagnosis of diseases (e.g., cardiac or pulmonary diseases), in accordance with some embodiments. System 1001 includes the same or similar components as system 1000 in FIG. 1A, however, the GDC 1010 and the AC 1020 in system 1001 are collocated in the same physical facility 1070 (e.g., a building).

Figure 1C:
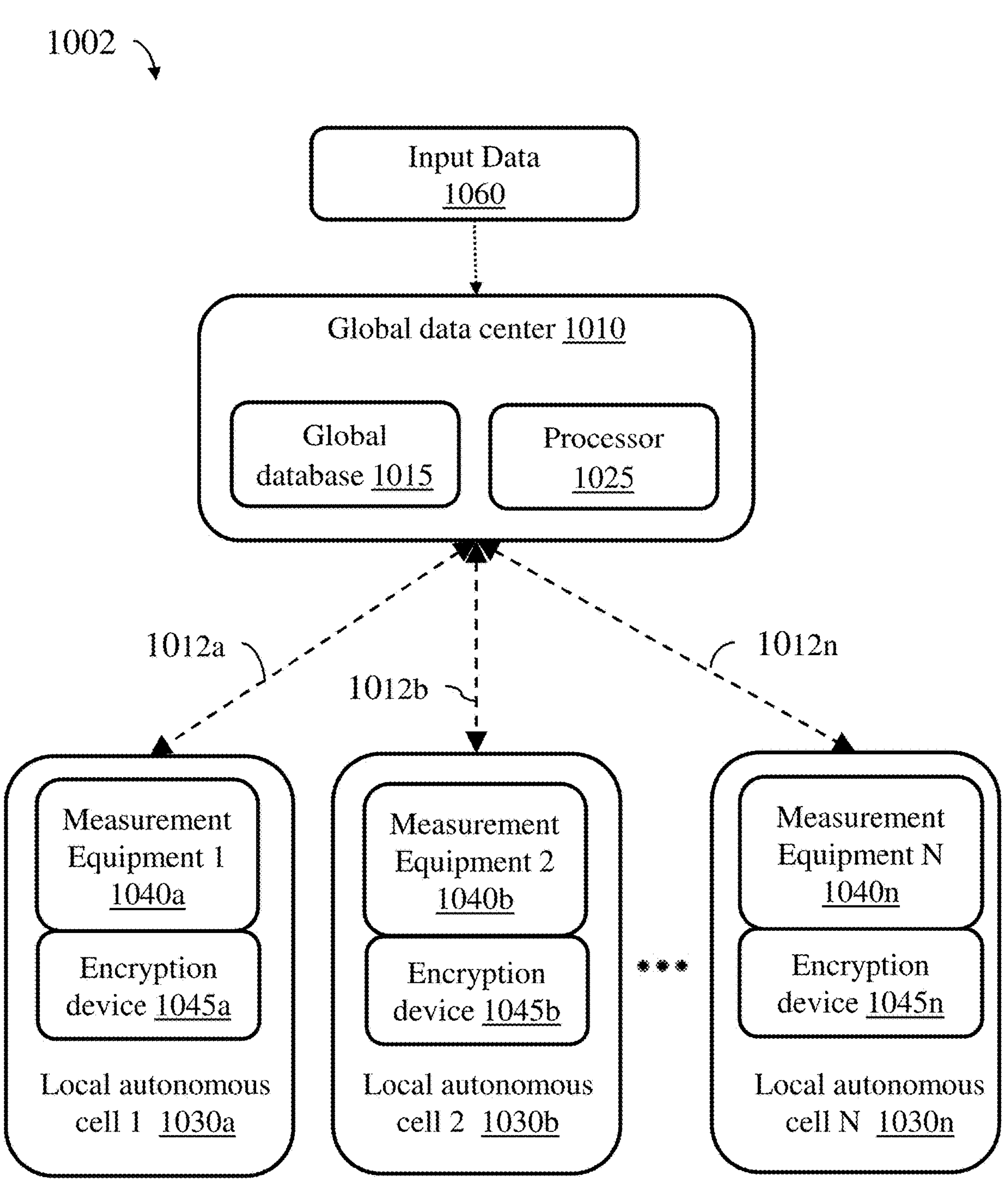

FIG. 1C shows a schematic of an example system 1002 for diagnosis of diseases (e.g., cardiac or pulmonary diseases), in accordance with some embodiments. System 1002 includes the same or similar components as system 1000 and 1001 in FIGS. 1A and 1B, however, there is no AC in system 1002. Instead, GDC 1010 includes a processor 1025 that can perform the same or similar functions as the processor of the AC 1020 in systems 1000 and 1001 described herein. The processor 1025 can be a single local computer, or more than one computer in a local network, or processor 1025 can be located in the cloud (i.e., processor 1025 can be located remotely from the GDC 1010, and, for example, be configured to perform cloud computing or to process data from the GDC 1010, for example, using a distributed network of computers) similar to processor 1090 in FIG. 1A.

Figure 1D:
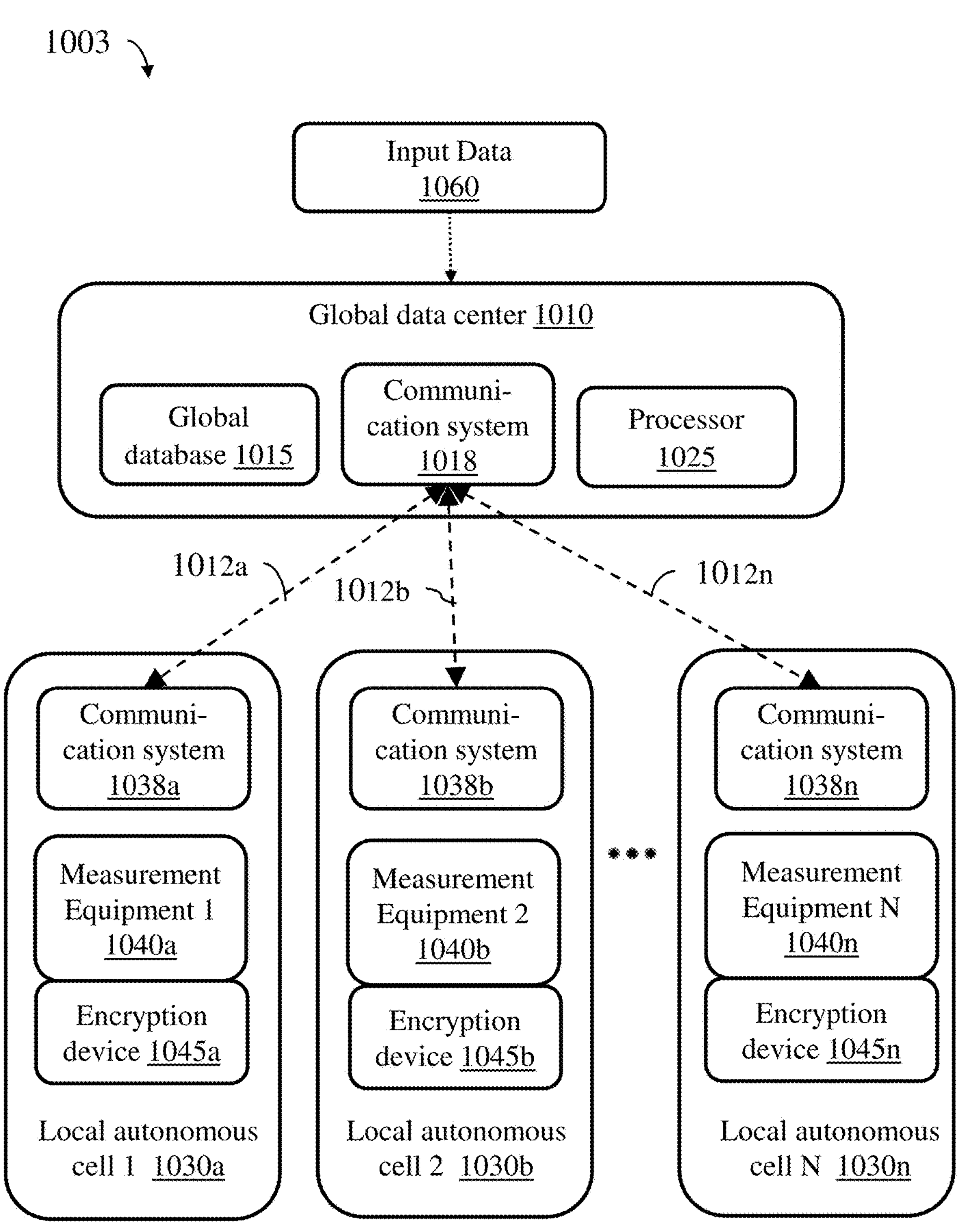

FIG. 1D shows a schematic of an example system 1003 for diagnosis of diseases (e.g., cardiac or pulmonary diseases), in accordance with some embodiments. System 1003 includes the same or similar components as system 1000, 1001 and 1002 in FIGS. 1A-1C. In this example, GDC 1010 and each of the LACs 1030*a*, 1030*b* and 1030*n* have respective communication systems 1018, 1038*a*, 1038*b* and 1038*n*. LAC communication systems 1038*a*, 1038*b* and 1038*n* are coupled to GDC communication system 1018 using respective communication channels 1012*a*, 1012*b* and 1012*n*. Communication channels 1012*a*, 1012*b* and 1012*n* can be capable of transferring data and information between the LACs 1030*a*, 1030*b* and 1030*n* and the GDC 1010, for example using a telecommunication network.

Systems 1000, 1001, 1002 and 1003 are shown with a number (N) of LACs (as indicated by the ellipsis between LAC 1030*b* and 1030*n*). Systems 1000, 1001, 1002 and 1003 can include more or less than three LACs. For example, systems 1000, 1001, 1002 and 1003 can include 1, 2, 3, 4, 5, 6, 7, 8, 9, 10, 20, 30, 40, 50, 60, 70, 80, 90, 100, 150, 200, 250, 300, 350, 400, 450, 500, or more than 500 LACs which comprise measurement equipment, each operatively coupled to a local computer. In some instances, systems 1000, 1001, 1002 and 1003 can include at most about 500, 450, 400, 350, 300, 250, 200, 150, 100, 90, 80, 70, 60, 50, 40, 30, 20, 10, 9, 8, 7, 6, 5, 4, 3, 2, or fewer than 2 LACs. In some instances, the number (N) of LACs in the system may range between any two of the values specified in this paragraph. For example, in some instances, the number of LACs in the system may range from 4 to 100. The number of LACs can have any value within the range of values specified in this paragraph, e.g., 125 local autonomous cells.

In some instances, systems 1000, 1001, 1002 and 1003 can include 1, 2, 3, 4, 5, 6, 7, 8, 9, 10, 20, 30, 40, 50, 60, 70, 80, 90, 100, 150, 200, 250, 300, 350, 400, 450, 500, or more than 500 measurement equipment units. In some instances, systems 1000, 1001, 1002 and 1003 can include at most about 500, 450, 400, 350, 300, 250, 200, 150, 100, 90, 80, 70, 60, 50, 40, 30, 20, 10, 9, 8, 7, 6, 5, 4, 3, 2, or fewer than 2 measurement equipment units. In some instances, the number (N) of measurement equipment units in the system may range between any two of the values specified in this paragraph. For example, in some instances, the number of measurement equipment units may range from 4 to 100. The number of measurement equipment units may have any value within the range of values specified in this paragraph, e.g., 125 measurement equipment units.

The measurement equipment 1040*a*, 1040*b*, and 1040*n* of systems 1000, 1001, 1002 and 1003 can be located in two or more different geographic locations. For example, a first measurement equipment unit in a first location can send one set of local measurement data and local patient data to the one or more computer processors of the GDC 1010 or the AC 1020 while a second measurement equipment unit in a second location can send a second set of local measurement data and local patient data to the system for processing by the one or more computer processors of the GDC 1010, the cloud, or the AC 1020. In some cases, the local patient data and the local measurement data can both be used to refine the data analytics algorithm of the GDC 1010 or the AC 1020 that generates computer-aided diagnostic indicators, and may also both be retained on the global database 1015 of the GDC 1010.

In some cases, systems 1000, 1001, 1002 and 1003 further comprise encryption device(s) 1045*a*, 1045*b* and 1045*n* coupled to the measurement equipment 1040*a*, 1040*b* and 1040*n*. In some cases, encryption device(s) 1045*a*, 1045*b* and 1045*n* can each include a global positioning system (GPS) positioning sensor configured to encrypt the local measurement data and local patient data and to track a location of the measurement equipment 1040*a*, 1040*b* and/or 1040*n*. In some cases, one or more of the measurement equipment 1040*a*, 1040*b*, and 1040*n* can include a data encryption device. The data encryption device can include a global positioning system (GPS) positioning sensor. The data encryption device may generate encrypted local measurement data, patient data, or any combination thereof. The encrypted local measurement data, patient data, or any combination thereof may be stored locally and/or transferred (or communicated) to the GDC 1010. The encrypted local measurement data, patient data, or any combination thereof can include data regarding changes in a location of measurement equipment coupled to the data encryption device. For example, image metadata for local measurement data can comprise location information for the measurement equipment that measured the data. In this example, a movement of the measurement equipment from one geographic location to another can be tracked using the image metadata transmitted by the measurement equipment. In another example, the GPS positioning sensor can be in constant communication with systems 1000, 1001, 1002 and 1003 (e.g., with a computer of an LAC 1030*a*, 1030*b* or 1030*n*, or with the GDC 1010) and the computer database regarding the location of the measurement equipment. The inclusion of the GPS sensor may reduce a likelihood that the measurement equipment is stolen or misappropriated by untrained users. The data encryption device can include a module configured to only permit communication between the measurement equipment and the systems 1000 or 1001 (e.g., with a computer of an LAC 1030*a*, 1030*b* or 1030*n*, or with the GDC 1010). For example, other network communications can be disabled such that the local measurement data can be sent only to the system systems 1000, 1001, 1002 and 1003 (e.g., to a computer of an LAC 1030*a*, 1030*b* or 1030*n*, or with the GDC 1010).

In some instances, the plurality of measurement equipment 1040*a*, 1040 and 1040*n* of systems 1000, 1001, 1002 and 1003 may be located in 2, 3, 4, 5, 6, 7, 8, 9, 10, 20, 30, 40, 50, 60, 70, 80, 90, 100, 150, 200, 250, 300, 350, 400, 450, 500, or more than 500 different geographical locations (thereby effectively constituting a global diagnostic system). In some instances, the number of different geographical locations comprising measurement equipment 1040*a*, 1040 and 1040*n* can range between any two of the values specified in this paragraph. For example, in some instances, the number of different geographical locations included may range from 8 to 20. The number of different geographical locations included can have any value within the range of values specified in this paragraph, e.g., 14 different geographical locations.

In some cases, the measurement equipment 1040*a*, 1040 and 1040*n* are portable. For example, each measurement equipment 1040*a*, 1040 and 1040*n* can be portable equipment to collect blood, urine, or tissue samples. In such cases, the samples could also be analyzed by the measurement equipment 1040*a*, 1040 and 1040*n*, or the samples can be provided to an LAC 1030*n* for analysis. In another example, each measurement equipment 1040*a*, 1040 and 1040*n* can be a portable electrocardiograph machine including: an electrical control module; a device for collecting an ECG; a mobile data base station; and a mobile digital display terminal.

In some cases, the measurement equipment 1040*a*, 1040 and 1040*n* of systems 1000, 1001, 1002 and 1003 are wearable. For example, each measurement equipment 1040*a*, 1040 and 1040*n* can be a wearable electrocardiograph machine including: an electrical control module; a device for collecting an ECG; and a device (or system within the device) for wireless transmission of ECGs to the local autonomous cell.

In some cases, systems 1000, 1001, 1002 and 1003 can include more than one GDC and/or more than one AC (not shown). For example, medical information can sometimes be restricted from leaving a certain country or region, and each such country or region can contain their own GDC and/or AC to prevent data from the global database and/or the LACs from leaving the country or region. In some cases, the LACs 1030*a*, 1030*b* and 1030*n* can be in communication with one GDC or with more than one GDC (e.g., from 1 to 10 GDCs). In some cases, systems 1000, 1001, 1002 and 1003 can include more than one GDC, some of the LACs 1030*a*, 1030*b* and 1030*n* can communicate with one of the GDCs, and other of the LACs 1030*a*, 1030*b* and 1030*n* can communicate with a different GDC. In some cases, systems 1000, 1001, 1002 and 1003 can include more than one GDC and one of the LACs 1030*a*, 1030*b* and 1030*n* can communicate with more than one GDC. In some cases, systems 1000, 1001, 1002 and 1003 can include more than one GDC and each of the LACs 1030*a*, 1030*b* and 1030*n* (or some of the LACs 1030*a*, 1030*b* and 1030*n*) can communicate with more than one GDC.

Figure 1E:
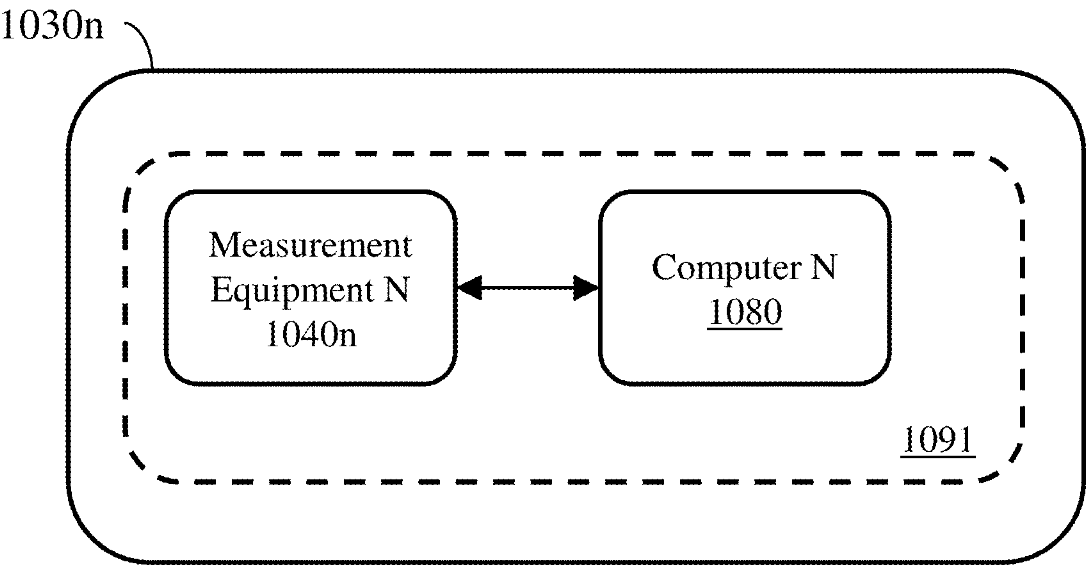
FIG. 1E shows an example of a local autonomous cell (LAC) including a facility containing measurement equipment, in accordance with some embodiments.

FIG. 1E shows an example of an LAC 1030*n* of systems 1000, 1001, 1002 and 1003 including a facility 1091 containing the measurement equipment 1040*n* and a computer 1080. Computer 1080 can be coupled to and can control measurement equipment 1040*n*. Computer 1080 can also be coupled to a local storage medium or cloud storage to store data (e.g., the local measurement data and/or local patient data). Computer 1080 can also contain a communication device configured to communicate with the GDC 1010 (e.g., using a telecommunication network). Computer 1080 can also be configured to prepare data (e.g., the local measurement data and/or local patient data) to be sent to the GDC 1010 (e.g., via mail), for example, by saving the data to a storage medium (e.g., a flash drive) and/or printing hard copies of the data for shipping.

In some cases, a measurement equipment 1040*a*, 1040*b* or 1040*n* associated with an LAC 1030*a*, 1030*b* or 1030*n* can be located in a geographical location that is different from a local computer of the LAC that is in communication with the measurement equipment 1040*a*, 1040*b* or 1040*n*. For example, measurement equipment 1040*n* can be portable and can be brought to a patient to take a measurement or a sample. In such cases the measurement equipment 1040*n* can communicate with a computer of LAC 1030*n* (e.g., in real-time, or in substantially real-time), or the measurement data or samples can be delivered to the LAC 1030*n* using another method (e.g., saved on a DVD or flash drive (e.g., memory stick) and sent by mail). In some cases, measurement equipment 1040*n* can be wearable, and can be worn by a patient throughout the day and can be associated with LAC 1030*n* and can communicate with a computer of LAC 1030*n* (e.g., in real-time, or in substantially real-time). In other cases, the measurement data or samples can be delivered to the LAC 1030*n* using another method (e.g., saved on a DVD or flash drive and sent by mail). Therefore, a single LAC can have components that are distributed over more than one geographical area. In some cases, the local patient is physically located close to a facility (e.g., a building or a trailer) housing a computer of the LAC. In such cases the local patient can have their local measurement data measured by measurement equipment located in the facility of the LAC and/or have their local measurement data measured by measurement equipment located outside the facility of the LAC (e.g., a wearable electrocardiograph machine for a Holter test). In other cases, the local patient can be physically located far from a facility (e.g., a building or a trailer) housing a computer of the LAC. In such cases the local patient can still benefit from using systems 1000, 1001, 1002 and 1003, and can have their local measurement data measured by measurement equipment located outside the facility of the LAC (e.g., located in another facility, or wearable measurement equipment) which is in communication with the computer of the LAC. In such cases, all of the local measurement data and local patient data can be communicated to the LAC (e.g., using mail, airmail or courier mail, e-mail, and/or using electronic information transfer means (e.g., one or more networks)).

Figure 1F:
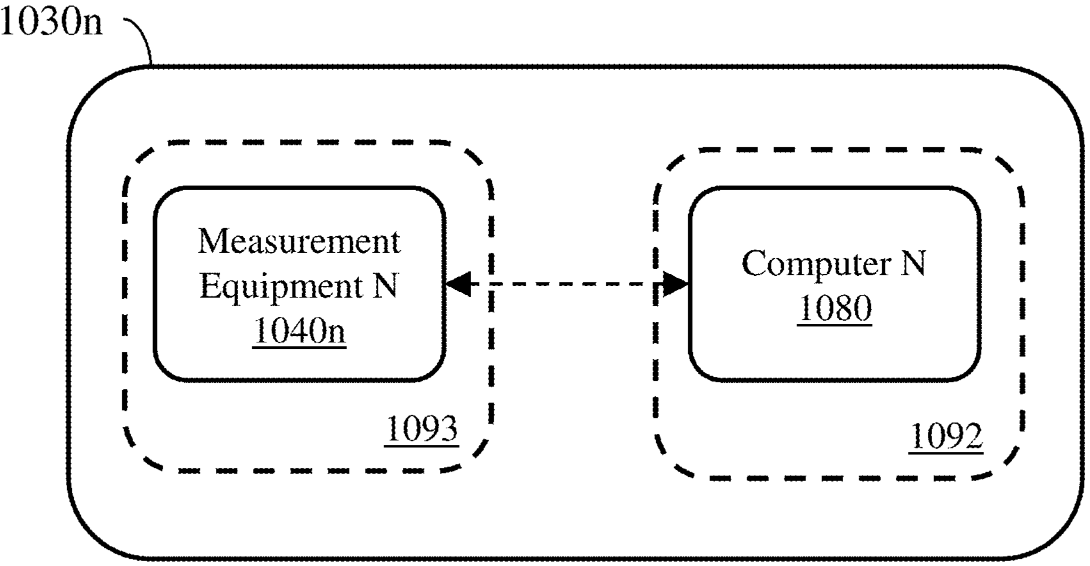
FIG. 1F shows an example of a local autonomous cell (LAC) including a first physical location (e.g., a facility, or building, or computer center) containing a computer, and a second physical location containing the measurement equipment, in accordance with some embodiments.

FIG. 1F shows an example of an LAC 1030*n* of systems 1000, 1001, 1002 and 1003 including a first physical location 1092 (e.g., a facility, or building, or computer center) containing a computer 1080, and a second physical location 1093 containing the measurement equipment 1040*n*. Measurement equipment 1040*n* can communicate with computer 1080, and send data (e.g., the local measurement data and/or local patient data) from the local patient being measured at physical location 1093 to the computer 1080 at physical location 1092. Computer 1080 can also be coupled to a local storage medium or cloud storage to store data (e.g., the local measurement data and/or local patient data) received. Computer 1080 can also contain a communication device configured to communicate with the GDC 1010 (e.g., using a telecommunication network). Computer 1080 can also be configured to prepare data (e.g., the local measurement data and/or local patient data) to be sent to the GDC 1010 (e.g., via mail), for example, by saving the data to a storage medium (e.g., a flash drive) and/or printing hard copies of the data for shipping.

In some embodiments, diagnostic systems 1000, 1001, 1002 and 1003 include a plurality of measurement equipment 1040*a*, 1040*b* and 1040*n* operatively coupled to GDC 1010 and/or the AC 1020 for computer processing of data over a network. The plurality of measurement equipment 1040*a*, 1040*b* and 1040*n* can be operatively coupled to the GDC 1010 and/or the AC 1020 for computer processing of data over a network.

The diagnostics systems 1000, 1001, 1002 and 1003 may include the global data center 1010, which includes a global database 1015. The global database 1015 may be configured to store data (e.g., local measurement data, patient data, or any combination thereof). The global database 1015 may be encrypted. The global database 1015 may be configured for compliance with health data privacy laws and regulations (e.g., HIPAA). The global database 1015 may be stored locally to the GDC 1010 and/or be stored in a distributed computer database (e.g., a cloud-based database housed at a plurality of locations). The global database 1015 may be configured to accept input data 1060 from one or more measurement equipment (of system 1000, 1001, 1002 or 1003, or from another source).

The GDC 1010, the cloud, and/or the AC 1020 contains one or more computer processors configured to process data. The one or more computer processors may be configured to pre-process, process, and/or post-process the data as described herein. The one or more computer processors may be coupled to the global database 1015 of the GDC 1010 via a network (e.g., a local network, the internet, a virtual private network). For example, systems 1000, 1001, 1002 and 1003 can have at least about 1, 5, 10, 25, 50, 75, 100, 250, 500, 750, 1,000, 2,500, 5,000, 10,000, 50,000, 100,000 or more measurement equipment. The one or more measurement equipment may be at most about 100,000, 50,000, 10,000, 5,000, 2,500, 1,000, 750, 500, 250, 100, 75, 50, 25, 10, 5, or less measurement equipment units. The one or more measurement equipment (e.g., 1040*a* 1040*b* and 1040*n* in systems 1000, 1001, 1002 and 1003) may be one or more of a same type of measurement equipment, or one or more of different types of measurement equipment. The computer processor(s) of GDC 1010, the cloud, and/or AC 1020 may be configured to periodically refine and update a statistical and/or machine learning based data analytics algorithm using data stored in the global database 1015. For example, the data analytics algorithm may be updated every month, every week, every day, or every hour. In some instances, the computer processors of AC 1020 and the global database 1015 may be configured to continually refine a statistical and/or machine learning based data analytics algorithm. For example, each time new data is received from a measurement equipment unit, the computer processors of AC 1020 can access that new data from the global database 1015 to update the data analytics algorithm. The data analytics algorithm may be a data analytics algorithm and/or machine learning algorithm as described herein.

The global diagnostics systems 1000, 1001, 1002 and 1003 can include one or more LACs 1030*a*, 1030*b* and 1030*n* which respectively can each include one or more measurement equipment 1040*a*, 1040*b* and 1040*n* operatively coupled to data storage devices (e.g., local data storage devices or cloud-based storage devices). Local measurement data, local patient data, or any combination thereof can be saved in the data storage devices before being transmitted from the LAC(s) 1030*a*, 1030*b* or 1030*n* to the GDC 1010, and optionally from the GDC 1010 to the AC 1020 for processing. The AC 1020 can then optionally transmit the appropriate diagnostic indicator to the GDC 1010, and the GDC 1010 can communicate the diagnostic indicator to the LAC(s) 1030*a*, 1030*b* or 1030*n* (e.g., by mail, airmail, courier mail, e-mail, or by electronic data transfer over a telecommunications network). The global diagnostics systems 1000, 1001, 1002 and 1003 can process and update the global database 1015 with local measurement data, patient data or any combination thereof, accumulated in LACs 1030*a*, 1030*b* or 1030*n* and delivered from LACs 1030*a*, 1030*b* or 1030*n* to the GDC by mail, airmail, courier mail, e-mail, or by electronic data transfer over a telecommunications network.

Figure 2:
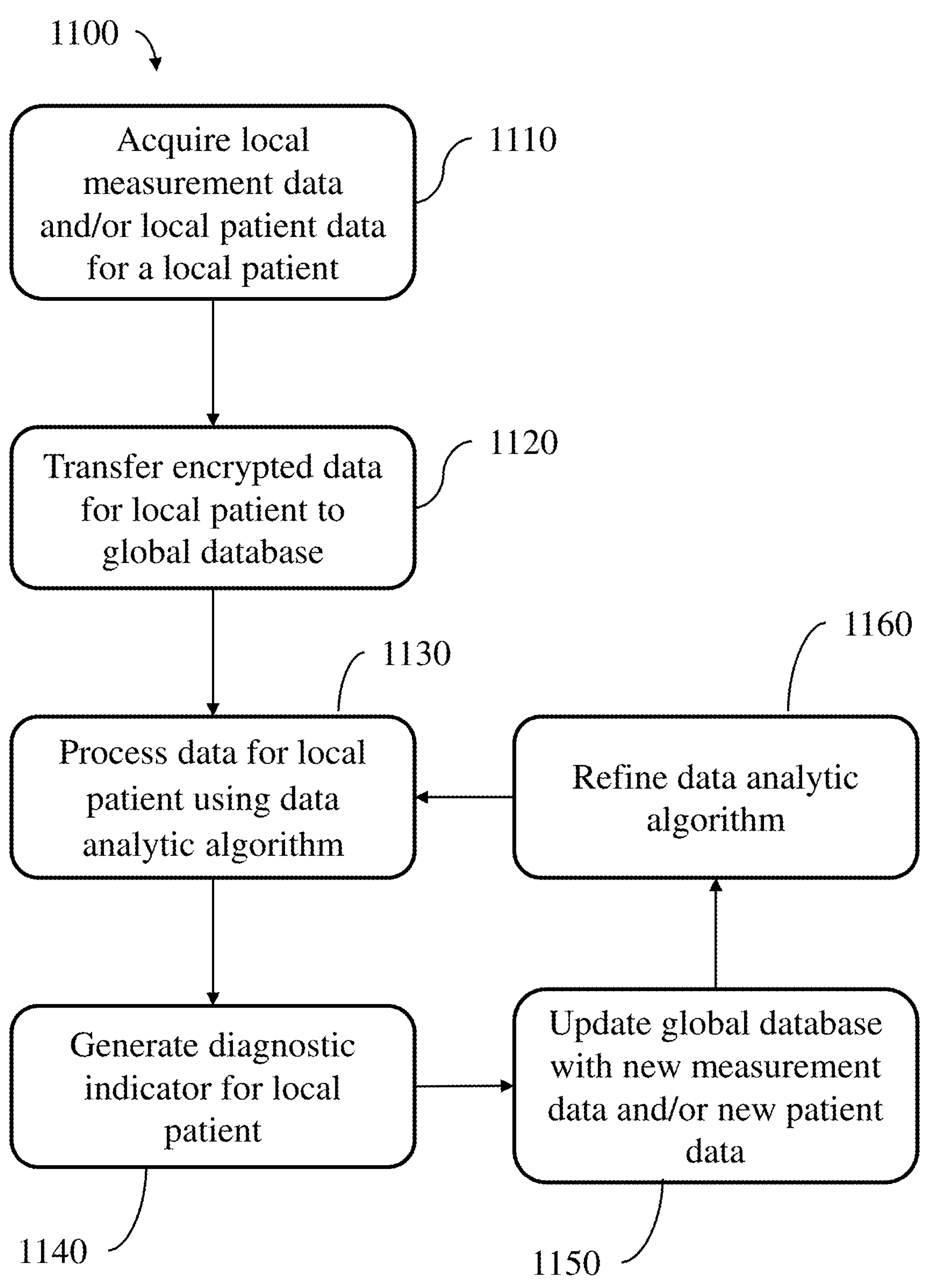
FIG. 2 shows a schematic of an example process for diagnosing diseases using the global diagnostic systems described herein, in accordance with some embodiments.

FIG. 2 shows a schematic of an example process 1100 for diagnosing diseases using the diagnostic systems described herein, in accordance with some embodiments. For example, systems 1000, 1001, 1002 or 1003 of FIGS. 1A-1F can be used to perform process 1100.

In block 1110, data for a local patient, for example including local measurement data, local patient data, or any combination thereof, is acquired. The local measurement data from the local patient can be acquired in a single session, either in person (e.g., at an LAC) or remotely (e.g., using a UI, as described herein). In other cases, the local measurement data from the local patient can be acquired over a plurality of sessions, or over a period of time (e.g., if the local patient is wearing an electrocardiograph machine for the period of time). For example, a time series of local measurement data (e.g., data from a tissue diffractometer) can be taken over a period of time to track a change in a condition or disease (e.g., an arrhythmia and violation of the heart rate state) of the local patient. The local measurement data, patient data, or any combination thereof may be data as described herein. The acquiring may be performed by one or more measurement equipment (e.g., of an LAC) as described herein. The local patient data can include one or more of: descriptions or data related to symptoms of the local patient comprising one or more of sleep disorders, insomnia, sudden awakenings, somnambulism, apnea, disorders of cerebral circulation, electroencephalogram (EEG) data, sudden convulsions and fainting, headaches and dizziness, and traumatic brain injuries and symptoms thereof. The local patient data can also include one or more of: age, gender, profession, blood pressure, body weight, body-mass index (BMI), cholesterol, cooccurrence of neurological diseases, registration in a cardio-dispensary, patient ethnicity, genetic data, and behavioral data, symptoms, reports from the patient, reports of discomfort, reports of chest pain, reports of back pain, reports of shortness of breath, leg swelling, information about chest injury, information about sustained hypertension, reports of constant and severe upper abdominal pain, and any other information related to the local patient.

In block 1120, encrypted data for the local patient is transferred to the global database (of the GDC). The encrypted data may include the local measurement data, patient data, or any combination thereof for one or more local patients. For example, the encrypted data can comprise all of the data taken from a veterinary clinic (or LAC) in a day. The encrypted data may be encrypted using an asymmetric key encryption, a symmetric key encryption, or the like. The encrypted data may be encrypted by a computing device local to where the data was generated (e.g., a computer operatively coupled to measurement equipment at an LAC). The encrypted data may be stored locally (e.g., at the LAC) before being transferred to the global database. The encrypted data may be streamed (e.g., transferred in real-time or substantially real-time over a telecommunications network) to a local database and/or to the global database. The local database can be stored on a local computing cluster housed in the same facility as where the data was acquired, or on a remote computer database (e.g., a cloud computing database operatively coupled to an LAC). The encrypted data may be uncompressed data or compressed data.

In another block 1130, the local data for the local patient is processed using a data analytics algorithm. The processing can be performed on one or more computer processors of the GDC, the cloud, and/or the AC, as described herein. The processing may be encoded on a non-transitory computer readable medium. The data analytics algorithm may be a statistical analysis algorithm and/or a machine learning algorithm. The data analytics algorithm may be a convolutional neural network as described herein. The data analytics algorithm may perform pre-processing, processing, and/or post-processing of local measurement data, patient data, or any combination thereof. The pre-processing can include denoising (e.g., removing noise from the data), normalizing (e.g., standardizing data properties such as size, black level, maximum intensity, etc.), segmentation (e.g., dividing the data into sections comprising different features), masking (e.g., applying one or more masks to the data), enhancing edges and/or features, or the like, or any combination thereof. The processing can include determining a presence or absence of a feature in the data, clustering data (e.g., clustering data based on the presence or absence of a feature), predicting a presence or absence of a feature in new data (e.g., using previously acquired data to generate a prediction of a presence of a feature in a new set of data), or the like, or any combination thereof. The post-processing can include formatting, denoising, normalizing, masking, enhancing properties (e.g., contrast, edges), or the like, or any combination thereof.

In block 1140, a diagnostic indicator for the local patient is generated. The diagnostic indicator may be a computer-aided diagnostic indicator generated using the processor of the GDC or the AC, as described herein. The computer-aided diagnostic indicator may be a computer readable report, a human readable report, or both. For example, the computer aided diagnostic indicator can be a report displayed on a user interface of a device. The diagnostic indicator can include information about a likelihood of a presence of a feature in the data. The diagnostic indicator can relate to one of more of: breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of the heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extra-cerebral tumors, bacterial endocarditis (inflammation of the inner lining of the heart), and meningococcal meningitis (inflammation of the membranes of the brain and spinal cord). In other examples, the diagnostic indicator can relate to one of more of: a presence of arrhythmia and violation of the heart rate (tachycardia, parasystole), diagnose failures in conducting nerve impulses inside the heart, identify acute and chronic changes (myocardial infarction, coronary heart disease), identify acute and chronic lung diseases (thromboembolism, chronic bronchitis), diagnose changes in myocardium, or thinning or thickening of the heart muscle, diagnose myocarditis (dangerous inflammation of the heart muscle), a severity of a presence of a feature (e.g., a prognosis based on the severity of the feature), one or more suggested treatments, additional information (e.g., locations of resources to help the patient understand the diagnostic indicator), patient data (e.g., the name of the local patient), or the like, or any combination thereof. The diagnostic indicator may be generated on the same computer system as the data analytics algorithm (e.g., at the GDC, in the cloud, or at the AC). The diagnostic indicator may be held until the local patient's owner or their veterinary services provider provides an input. The input may be a payment (e.g., a payment from the patient, a payment from the patient's insurance), an agreement for the local patient data to be used for training and/or validating future data analytics algorithms, or the like, or any combination thereof. For example, the local patient's owner can be informed that the diagnostic indicator is ready, and that the patient's owner can sign a waiver allowing use of the patient data.

In block 1150, the global database is updated with new measurement data, new patient data, or any combination thereof. The new measurement data and/or new patient data can be generated for a plurality of patients using a plurality of measurement equipment, and can be stored in the global database, for example. The updating may make additional data available to train a new data analytics algorithm or update an existing data analytics algorithm. In some cases, the global database may be updated with indicators of a confirmation of an indication made in a diagnostic indicator (e.g., indicators about how accurate the diagnostic indictors were for a sample study). For example, the global database can be updated with information regarding the confirmation of a condition or disease (e.g., an arrhythmia and violation of the heart rate (tachycardia, parasystole)). This updating may provide confirmation of positive or negative results that can improve the accuracy of future diagnostic indicators. The new data may be agglomerated for the plurality of patients to generate a general classifier. For example, a database of data from a tissue diffractometer can be used to generate a classifier for acute and chronic changes (e.g., myocardial infarction, or coronary heart disease). In another example, a global database of global data can be used to generate a classifier to diagnose changes in a condition or disease (e.g., changes in myocardium, or thinning or thickening of the heart muscle).

In block 1160, the data analytics algorithm is refined. The refining may include generating a new data analytics algorithm based on an analysis of the updated global database (of block 1150). The refining can include updating weights or other components within the data analytics algorithm. For example, the neural weights of a neural network can be updated based on the new data in the updated global database. The refining of the data analytics algorithm may improve the sensitivity, specificity, accuracy, or any combination thereof of the data analytics algorithm and/or of the diagnostics indicators generated using the data analytics algorithm.

Process 1100 in FIG. 2 also shows that the refined data analytics algorithm can be used to process local data for another patient (e.g., used as the data analytics algorithm) in a subsequent instance of block 1130.

Figure 3A:
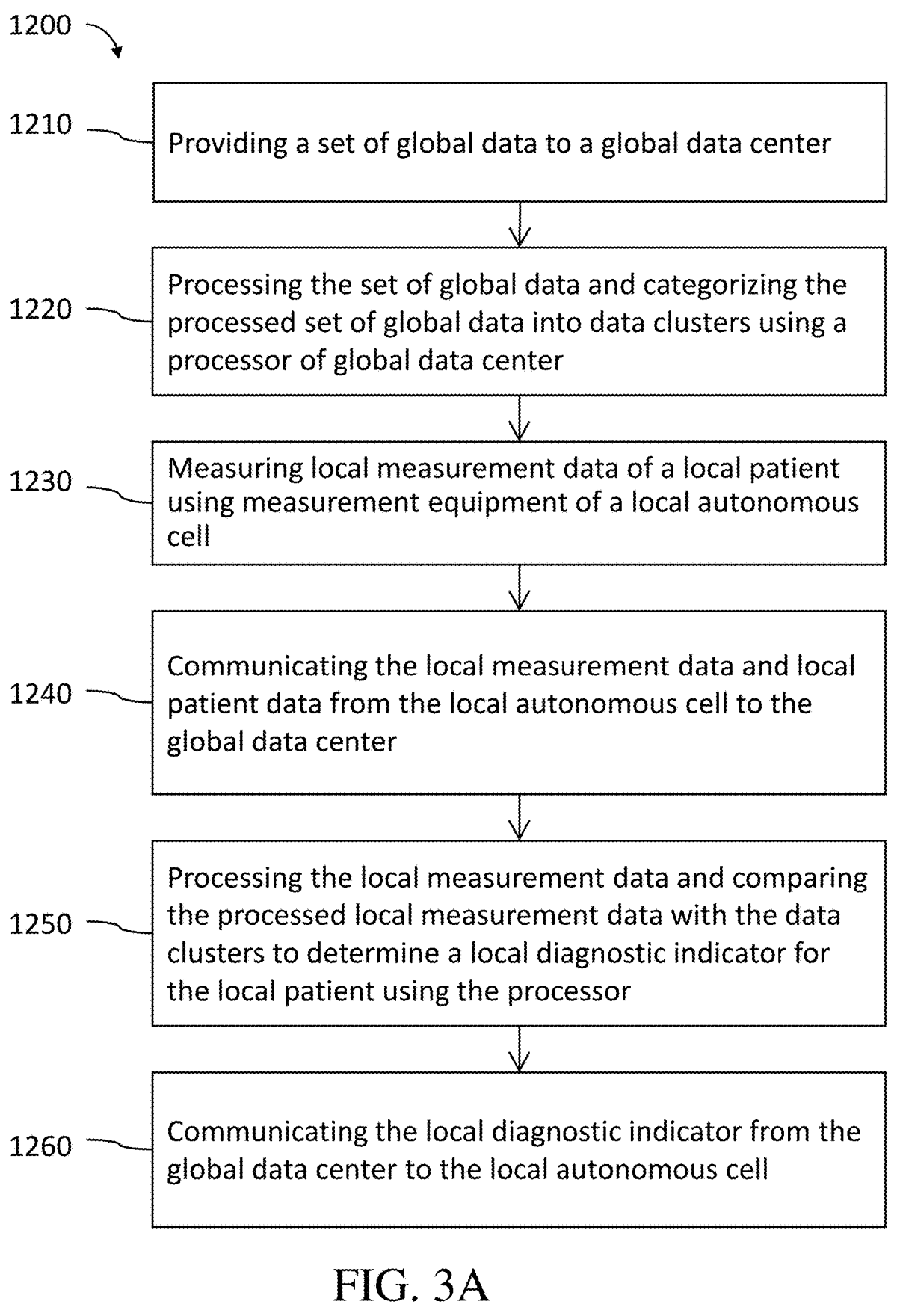

FIG. 3A shows an example method 1200 for diagnosing diseases (e.g., cancer, lung disease, cardiac diseases, or any of the diseases described herein), in accordance with some embodiments. In block 1210 of method 1200, a set of global data is provided to a global data center (GDC), and optionally to an analytical center (AC). The set of global data is from a set of patients, and may have a set of patient data for the set of patients associated with the set of global data. For example, the global data can include a set of data from one or more tissue diffractometers, and the set of patient data can include diagnoses of diseases or conditions, information about one or more pieces of data of the set data from the one or more tissue diffractometers, patient outcomes, or other information that may be used to classify the data from the one or more tissue diffractometers. In block 1220, the set of global data is processed, and the processed set of global data is categorized into data clusters using a processor of the GDC, the cloud, or the AC. In some cases, each data cluster corresponds to a diagnostic indicator for assessment of a physiological or pathological condition (e.g., any of the diseases or conditions described herein).

In block 1230 of method 1200, local measurement data of a local patient is measured using measurement equipment of a local autonomous cell (LAC). In block 1240, the local measurement data and local patient data is communicated from the LAC to the GDC, and optionally from the GDC to the AC. In some cases, more than one LAC can measure local measurement data of local patients (that are local to each of the LACs) each using measurement equipment. Each LAC can then communicate one or more local measurement data to the GDC. The communication between the LAC(s) and the GDC can be done using any means, for example, mail, airmail, courier mail, e-mail, or by transferring data electronically (e.g., over a telecommunications network). This can be advantageous, for example, so that the one or more LACs do not need to have an internet connection for the method to be carried out. For example, one or more LACs can be located in remote regions, developing regions, or regions after disasters, and the LACs can communicate with the GDC using available (e.g., non-electronic) means. The communication of information between the GDC and the AC can be done electronically (e.g., over a telecommunications network).

In block 1250 of method 1200, the local measurement data is processed and the processed local measurement data is compared with the data clusters to determine local diagnostic indicator(s) for the local patient(s) using the processor of the GDC, the cloud, and/or the AC. In block 1260, the local diagnostic indicator(s) are communicated, optionally from the AC to the GDC, and from the GDC to the LAC(s).

In some embodiments of method 1200, the set of global data is provided from a certain geographical region or nation (e.g., southeast United States, or Untied States). This can be advantageous, for example, because it can help more accurately diagnose the conditions for patients from that region or nation, compared to comparing the local measurement data to data from a different database that is less representative of the situation and/or environment of the local patient. In some embodiments of method 1200, there are a plurality of local autonomous cells in different geographic locations. For example, each LAC can be in a different geographic location, or two or more LACs can be in one location and other LACs can be in different geographic locations.

In some embodiments of method 1200, the GDC further comprises a global database residing on a central server or in the cloud, wherein the global database comprises the set of global data.

In some embodiments of method 1200, the local measurement data, the local patient data, or any combination thereof is depersonalized before communicating the local measurement data and the local patient data from the LAC to the GDC, for instance to protect patient privacy. In such cases, the communicating the local measurement data and the local patient data from the LAC to the GDC in block 1240 comprises communicating the depersonalized local measurement data and the depersonalized local patient data from the LAC to the GDC. Depersonalizing the information can include removing identifying characteristics from the information before sending from the LAC to the GDC, and providing a key or decoder by which the information can be associated with a patient by those with access to the key or decoder. In some cases, the key or decoder can be available to the patient or a veterinary service provider of the patient at the LAC.

In some embodiments of method 1200, the processing the set of global data and categorizing the processed the set of global data into data clusters comprises performing a statistical analysis on the processed set of global data. The statistical analysis can be performed using statistical algorithms, as described herein.

In some embodiments of method 1200, the processing the set of global data and categorizing the processed the set of global data into data clusters in block 1220 is done using a machine learning algorithm. In some cases, the processing of the local measurement data and comparing the processed local measurement data with the data clusters to determine a local diagnostic indicator for the local patient is done using a machine learning algorithm. The machine learning algorithm can include a supervised learning algorithm, an unsupervised learning algorithm, a semi-supervised learning algorithm, a reinforcement learning algorithm, a deep learning algorithm, or any combination thereof. The machine learning algorithm can include a convolutional neural network, a recurrent neural network, or a recurrent convolutional neural network. The machine learning algorithm can be trained using a training dataset comprising training measurement data, training patient data, or any combination thereof, wherein the training dataset comprises data from a set of training patients with known pathologies or physiological norm groups. The training dataset can also be updated with new training measurement data, new training patient data, or any combination thereof, upon the new training measurement data being added to the GDC.

In some embodiments of method 1200, the local patient data can include, for example, descriptions or data related to symptoms of the local patient comprising one or more of: sleep disorders, insomnia, sudden awakenings, somnambulism, apnea, disorders of cerebral circulation, electroencephalogram (EEG) data, sudden convulsions and fainting, headaches and dizziness, and traumatic brain injuries and symptoms thereof. The local patient data can also include, for example, one or more of: age, gender, profession, blood pressure, body weight, body-mass index (BMI), cholesterol, cooccurrence of neurological diseases, registration in a cardio-dispensary, patient ethnicity, genetic data, and behavioral data. The local patient data can also include one or more of: symptoms, reports from the local patient, reports of discomfort, reports of chest pain, reports of back pain, reports of shortness of breath, leg swelling, information about chest injury, information about sustained hypertension, and reports of constant and severe upper abdominal pain.

In some embodiments of method 1200, the diagnostic indicators can relate to one of more of: breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of the heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extracerebral tumors, bacterial endocarditis (inflammation of the inner lining of the heart), and meningococcal meningitis (inflammation of the membranes of the brain and spinal cord). In the case of heart-related conditions and diseases, the diagnostic indicators can relate to one of more of: detection of arrhythmia and heart rate violation, the detection of tachycardia, the detection of parasystole, diagnosing failures in conducting nerve impulses inside the heart, identification of acute and chronic changes, identification of myocardial infarction, identification of coronary heart disease, identification of acute and chronic lung diseases, identification of thromboembolism, identification of chronic bronchitis, diagnosis of changes in myocardium, diagnosis of heart muscle thinning, diagnosis of thickening of the heart muscle, diagnosis of myocarditis, and diagnosis of inflammation of the heart muscle.

In some embodiments of method 1200, the measurement equipment is portable. For example, each measurement equipment can be portable equipment to collect blood, urine, or tissue samples. In such cases, the samples could also be analyzed by the measurement equipment, or the samples can be provided to an LAC for analysis. In another example, each measurement equipment can be a portable electrocardiograph machine including: an electrical control module; a device for collecting an ECG; a mobile data base station; and a mobile digital display terminal.

In some embodiments of method 1200, the measurement equipment is wearable. For example, each measurement equipment can be a wearable electrocardiograph machine including: an electrical control module; a device for collecting an ECG; and a device (or system within the device) for wireless transmission of ECGs to the LAC(s).

In some embodiments, method 1200 further includes performing additional studies to compare to the diagnostic indicator, wherein the additional studies are one or more of: a general blood test, a blood test to assess troponin level, a urine test, a carotid arteries ultrasound examination, and communicating results of the additional studies from the LAC to the GDC. In some cases, the results of the additional studies are used by a veterinary service provider associated with the LAC to more accurately diagnose the local patient. In some cases, the results of the additional studies are provided to the GDC and AC for inclusion in the global database and/or for additional analysis. For example, the results of the additional studies could be used to further refine the categorization of the global data of the global database into data clusters. The results of the additional studies could also be used by the processor of the GDC, the cloud, and/or the AC to refine the determination of the diagnostic indicator for the local patient.

Figure 3B:
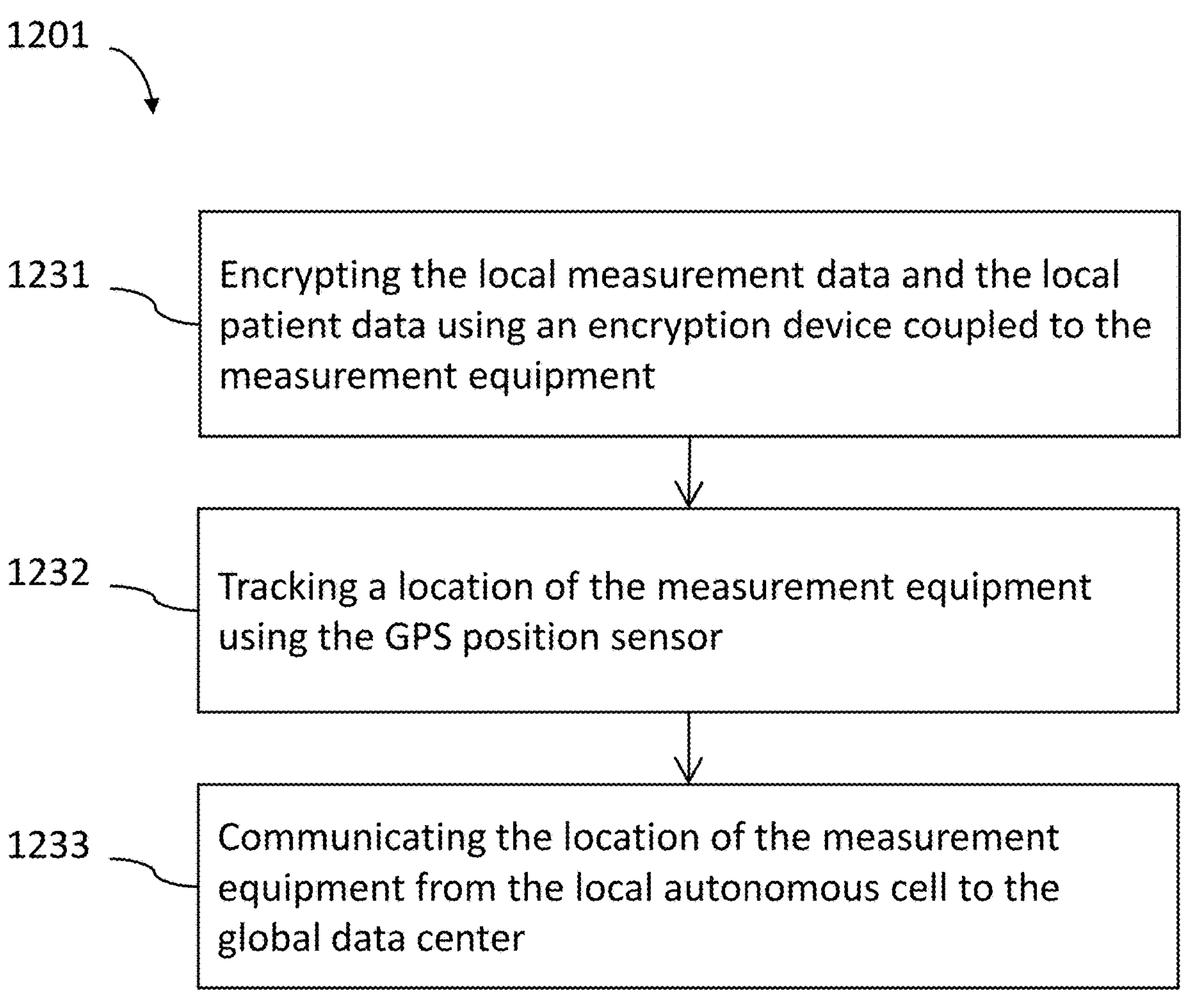
FIG. 3B shows an example method for diagnosing diseases that can optionally be performed in conjunction with the method of FIG. 3A, in accordance with some embodiments.

FIG. 3B shows an example method 1201 for diagnosing diseases (e.g., cardiac or pulmonary diseases) that can optionally be performed in conjunction with method 1200 in FIG. 3A. In block 1231 of method 1201 the local measurement data and the local patient data are encrypted using an encryption device coupled to the measurement equipment. Block 1231 can occur after block 1230 and before block 1240 in method 1200. When method 1201 is performed, then in block 1240 of method 1200 in FIG. 3A, the encrypted local measurement data and encrypted the local patient data can be communicated from the LAC to the GDC. The encryption device can include a global positioning system (GPS) positioning sensor. In block 1232, a location of the measurement equipment is tracked using the GPS position sensor. In block 1233, the location of the measurement equipment is communicated from the LAC to the GDC.

Figure 4:
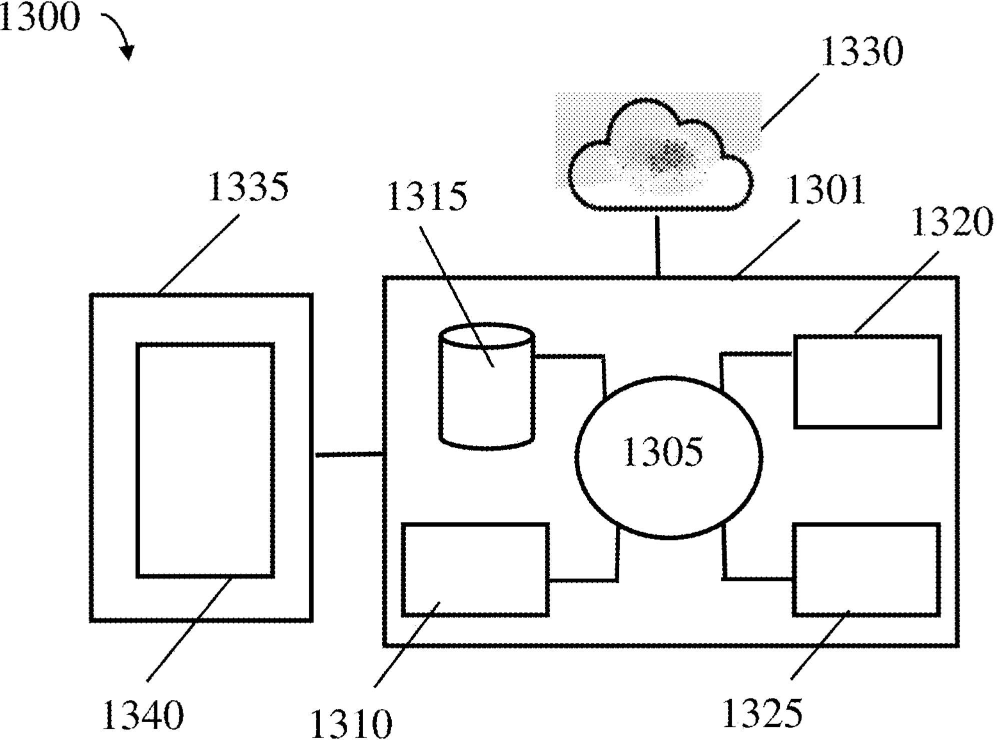
FIG. 4 shows a block diagram of a computer system that is programmed or otherwise configured to implement methods described herein, in accordance with some embodiments.

The present disclosure provides computer systems that are programmed to implement methods of the disclosure. FIG. 4 shows a system 1300 including a computer system 1301, a network 1330, and an electronic display 1335. The computer system 1301 is programmed or otherwise configured to implement methods described herein (e.g., obtaining data from measurement equipment, processing the data, etc.). The computer system 1301 can regulate various aspects of the present disclosure, such as controlling measurement equipment, and processing global data, local measurement data, patient data, or any combination thereof. The computer system 1301 can be an electronic device of a user or a computer system that is remotely located with respect to the electronic device. The electronic device can be a mobile electronic device. The computer system 1301 may be a post-classical computer system (e.g., a quantum computing system).

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

Methods and systems of the present disclosure can be implemented by way of one or more algorithms. An algorithm can be implemented by way of software upon execution by the CPU 1305. The algorithm can, for example, be a machine learning algorithm as described herein.

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user (e.g., a cloud server). Examples of remote computer systems include personal computers (e.g., portable PC), slate or tablet PCs (e.g., Apple® iPad, Samsung® Galaxy Tab), telephones, smart phones (e.g., Apple® iphone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine-readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processor adapted to execute the code, or can be compiled during runtime. The code can be supplied in a programming language that can be selected to enable the code to execute in a precompiled or as-compiled fashion.

Some aspects of the systems and methods provided herein, such as the computer system 1301, can be embodied in programming. Some aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory), or on a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the databases and the processes described herein. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340 for providing, for example, an interface for a healthcare worker or an individual patient's owner to upload local measurement data, patient data, or any combination thereof to a computer database. The UI can also provide an interface for a healthcare worker or an individual patient's owner to view local measurement data, patient data, or any combination thereof. Examples of UI's include, without limitation, a graphical user interface (GUI) and web-based user interface.

EMBODIMENTS

Clause 1. A method for diagnosing diseases in animal patients comprising: providing a set of global data to a global data center; processing the set of global data and categorizing the processed set of global data into data clusters using a processor coupled to the global data center, wherein each data cluster corresponds to a diagnostic indicator for assessment of a physiological or pathological condition; measuring a local measurement data of a local patient using measurement equipment of a local autonomous cell, wherein the local patient is an animal; communicating the local measurement data and local patient data from the local autonomous cell to the global data center; processing the local measurement data and comparing the processed local measurement data with the data clusters to determine a local diagnostic indicator for the local patient using the processor; and communicating the local diagnostic indicator from the global data center to the local autonomous cell.

Clause 2. The method for diagnosing diseases of clause 1, wherein the measurement equipment comprises one or more of an electrocardiograph machine, equipment for daily (Holter) monitoring, an echocardiograph machine, a magnetic resonance imaging (MRI) machine, a computerized tomography (CT) machine, equipment for blood analysis, equipment for urine analysis, liquid chromatography-mass spectroscopy equipment, a tissue diffractometer configured to perform small angle X-ray scattering (SAXS) measurements, a tissue diffractometer configured to perform wide angle X-ray scattering (WAXS) measurements, an electroencephalograph machine, atomic absorption spectroscopy (AAS), inductively coupled plasma optical emission spectroscopy (ICP-OES), and inductively coupled plasma mass spectrometry (ICP-MS).

Clause 3. The method for diagnosing diseases of clause 1, wherein the measuring the local measurement data comprises measuring a sample comprising $\alpha$-keratin or collagen.

Clause 4. The method for diagnosing diseases of clause 1, wherein the measuring the local measurement data comprises in vivo or in vitro measurement of a sample comprising hair, nail, skin, wool, horns, hooves, or tissue of an internal organ.

Clause 5. The method for diagnosing diseases of clause 1, wherein the set of global data is provided from a certain geographical region or nation.

Clause 6. The method for diagnosing diseases of clause 1, wherein the processor is in the cloud, and uses cloud computing to process data using a distributed network of computers.

Clause 7. The method for diagnosing diseases of clause 1, wherein the global data center comprises the processor.

Clause 8. The method for diagnosing diseases of clause 1, further comprising an analytical center in communication with the global data center, wherein the analytical center comprises the processor.

Clause 9. The method for diagnosing diseases of clause 1, further comprising: measuring a plurality of local measurement data of a plurality of local patients using a plurality of measurement equipment of a plurality of local autonomous cells, wherein: the local measurement data is one of the plurality of local measurement data; the local patient is one of the plurality of local patients; the measurement equipment is one of the plurality of measurement equipment; the local autonomous cell is one of the plurality of local autonomous cells; and a plurality of local patient data is associated with the plurality of local patients; communicating the plurality of local measurement data and the plurality of local patient data from the plurality of local autonomous cells to the global data center; processing the plurality of local measurement data using the processor; comparing the plurality of processed local measurement data with the data clusters to determine a plurality of local diagnostic indicators for the plurality of local patients; communicating the plurality of local diagnostic indicators from the global data center to the plurality of local autonomous cells.

Clause 10. The method for diagnosing diseases of clause 9, wherein local autonomous cells of the plurality of local autonomous cells are in different geographic locations.

Clause 11. The method of clause 1, further comprising providing a tissue sample from the local patient to the local autonomous cell to be measured using the measurement equipment.

Clause 12. The method of clause 11, wherein the tissue sample comprises one or more of a surgical sample, a resection sample, a pathology sample, or a biopsy sample.

Clause 13. The method of clause 11, wherein the tissue sample comprises one or more of hair, nail, skin, or tissue of an internal organ.

Clause 14. The method of clause 11, wherein the providing a tissue sample from the local patient to the local autonomous cell comprises the local patient or a veterinary services provider of the local patient using a user interface to input the local patient data and sending the tissue sample by mail.

Clause 15. The method for diagnosing diseases of clause 1, wherein the communicating the local measurement data and the local patient data from the local autonomous cell to the global data center is done by an owner of the local patient or a veterinary services provider of the local patient using a user interface.

Clause 16. The method for diagnosing diseases of clause 1, further comprising communicating the local diagnostic indicator from the local autonomous cell to an owner of the local patient or a veterinary services provider of the local patient using a user interface.

Clause 17. The method for diagnosing diseases of clause 1, further comprising encrypting the local measurement data and the local patient data using a data encryption device coupled to the measurement equipment, wherein the communicating the local measurement data and the local patient data from the local autonomous cell to the global data center comprises communicating the encrypted local measurement data and encrypted the local patient data from the local autonomous cell to the global data center.

Clause 18. The method for diagnosing diseases of clause 1, wherein the global data center further comprises a global database stored on a central server or in the cloud, wherein the global database comprises the set of global data.

Clause 19. The method for diagnosing diseases of clause 1, further comprising depersonalizing the local measurement data, the local patient data, or any combination thereof before communicating the local measurement data and the local patient data from the local autonomous cell to the global data center, wherein the communicating the local measurement data and the local patient data from the local autonomous cell to the global data center comprises communicating the depersonalized local measurement data and the depersonalized local patient data from the local autonomous cell to the global data center.

Clause 20. The method for diagnosing diseases of clause 19, wherein a key for mapping the depersonalized local measurement data, the local patient data, or any combination thereof is stored in a local institutional database or in an individual personal file of the patient.

Clause 21. The method for diagnosing diseases of clause 1, wherein the processing the set of global data and categorizing the processed the set of global data into data clusters comprises performing a statistical analysis on the processed set of global data.

Clause 22. The method for diagnosing diseases of clause 1, wherein the processing the set of global data and categorizing the processed set of global data into data clusters is done using a machine learning algorithm.

Clause 23. The method for diagnosing diseases of clause 1, wherein the local patient data comprises descriptions or data related to symptoms of the local patient comprising one or more of sleep disorders, insomnia, sudden awakenings, somnambulism, apnea, disorders of cerebral circulation, electroencephalogram (EEG) data, sudden convulsions and fainting, headaches and dizziness, and traumatic brain injuries and symptoms thereof.

Clause 24. The method for diagnosing diseases of clause 1, wherein the diagnostic indicators relate to one of more of breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of the heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extra-cerebral tumors, bacterial endocarditis (inflammation of the inner lining of the heart), and meningococcal meningitis (inflammation of the membranes of the brain and spinal cord).

Clause 25. The method for diagnosing diseases of clause 1, wherein the communicating the local measurement data and the local patient data from the local autonomous cell to the global data center is done by mail, airmail, courier mail or e-mail.

Clause 26. The method for diagnosing diseases of clause 1, wherein the communicating the local measurement data and the local patient data from the local autonomous cell to the global data center or the communicating the local diagnostic indicator from the global data center to the local autonomous cell occurs about once per day, or about once per week, or about once per month on average.

Clause 27. A system for diagnosis of diseases in animal patients comprising: a local autonomous cell comprising measurement equipment configured to measure local measurement data of a local patient, wherein the local patient is an animal; and a global data center in communication with the local autonomous cell, wherein the global data center comprises a set of global data stored in a global database; and a processor coupled to the global data center, the processor configured to: process the set of global data and categorize the processed set of global data into data clusters, wherein each data cluster corresponds to a diagnostic indicator for assessment of a physiological or pathological condition; and process the local measurement data and compare the processed local measurement data with the data clusters to determine a local diagnostic indicator for the local patient.

Clause 28. The system for diagnosis of diseases of clause 27, wherein the measurement equipment comprises one or more of an electrocardiograph machine, equipment for daily (Holter) monitoring, an echocardiograph machine, a magnetic resonance imaging (MRI) machine, a computerized tomography (CT) machine, equipment for blood analysis, equipment for urine analysis, liquid chromatography-mass spectroscopy equipment, a tissue diffractometer configured to perform small angle X-ray scattering (SAXS) measurements, a tissue diffractometer configured to perform wide angle X-ray scattering (WAXS) measurements, an electroencephalograph machine, atomic absorption spectroscopy (AAS), inductively coupled plasma optical emission spectroscopy (ICP-OES), and inductively coupled plasma mass spectrometry (ICP-MS).

Clause 29. The system for diagnosis of diseases of clause 27, wherein the measuring the local measurement data comprises measuring a sample comprising α-keratin or collagen.

Clause 30. The system for diagnosis of diseases of clause 27, wherein the measuring the local measurement data comprises in vivo or in vitro measurement of a sample comprising hair, nail, skin, wool, horns, hooves, or tissue of an internal organ.

Clause 31. The system for diagnosis of diseases of clause 27, wherein the set of global data is provided from a certain geographical region or nation.

Clause 32. The system for diagnosis of diseases of clause 27, wherein the processor is in the cloud, and uses cloud computing to process data using a distributed network of computers.

Clause 33. The system for diagnosis of diseases of clause 27, wherein the global data center comprises the processor.

Clause 34. The system for diagnosis of diseases of clause 27, further comprising an analytical center in communication with the global data center, wherein the analytical center comprises the processor.

Clause 35. The system for diagnosis of diseases of clause 27, further comprising a plurality of local autonomous cells comprising a plurality of measurement equipment configured to measure a plurality of local measurement data of a plurality of local patients, wherein the local measurement data is one of the plurality of local measurement data, the local patient is one of the plurality of local patients, the measurement equipment is one of the plurality of measurement equipment, and the local autonomous cell is one of the plurality of local autonomous cells, and wherein the processor is further configured to process the plurality of local measurement data and compare the processed plurality of local measurement data with the data clusters to determine a plurality of local diagnostic indicators for the plurality of local patients.

Clause 36. The system for diagnosis of diseases of clause 35, wherein local autonomous cells of the plurality of local autonomous cells are in different geographic locations.

Clause 37. The system for diagnosis of diseases of clause 27, further comprising providing a tissue sample from the local patient to the local autonomous cell to be measured using the measurement equipment.

Clause 38. The system for diagnosis of diseases of clause 37, wherein the tissue sample comprises one or more of a surgical sample, a resection sample, a pathology sample, or a biopsy sample.

Clause 39. The system for diagnosis of diseases of clause 37, wherein the tissue sample comprises one or more of hair, nail, skin, or tissue of an internal organ.

Clause 40. The system for diagnosis of diseases of clause 27, wherein the system further comprises a data encryption device coupled to the measurement equipment configured to encrypt the local measurement data and local patient data.

Clause 41. The system for diagnosis of diseases of clause 27, wherein the global database is stored on a central server or in the cloud.

Clause 42. The system for diagnosis of diseases of clause 27, wherein the processor is further configured to process the set of global data and categorize the processed set of global data into data clusters by performing a statistical analysis on the processed set of global data.

Clause 43. The system for diagnosis of diseases of clause 27, wherein the processor is further configured to process the set of global data and categorize the processed set of global data into data clusters using a machine learning algorithm.

Clause 44. The system for diagnosis of diseases of clause 27, wherein local patient data comprises descriptions or data related to symptoms of the local patient comprising one or more of sleep disorders, insomnia, sudden awakenings, somnambulism, apnea, disorders of cerebral circulation, electroencephalogram (EEG) data, sudden convulsions and fainting, headaches and dizziness, and traumatic brain injuries and symptoms thereof.

Clause 45. The system for diagnosis of diseases of clause 27, wherein the diagnostic indicators relate to one of more of breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of the heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extra-cerebral tumors, bacterial endocarditis (inflammation of the inner lining of the heart), and meningococcal meningitis (inflammation of the membranes of the brain and spinal cord).

Clause 46. The system for diagnosis of diseases of clause 27, wherein the local autonomous cell and the global data center are in communication by airmail, courier mail, or e-mail.

Clause 47. The system for diagnosis of diseases of clause 27, wherein the local autonomous cell (LAC) further comprises an LAC communication system, wherein the global data center (GDC) further comprises a GDC communication system, and wherein the LAC and the GDC communication systems are configured to electronically transfer information between the LAC and the GDC.

Clause 48. A system for diagnosis of cardiac diseases comprising: a local autonomous cell comprising local measurement equipment coupled to a local data storage device, wherein the local measurement equipment is configured to measure local measurement data of a local patient and the local data storage device is configured to store the local measurement data of the local patient and local patient data; a global data center comprising a global database, the global database comprising a set of global data from a set of patients; and a computer processor coupled to the global data center and configured to process the set of global data from the set of patients and to categorize them into data clusters, wherein each data cluster corresponds to a diagnostic indicator for assessments of a physiological or pathological condition; wherein the local patient is an animal, wherein the local measurement data of the local patient is provided from the local autonomous cell to the global data center, wherein the computer processor is further configured to process the local measurement data of the local patient and compare the processed local measurement data with the data clusters to determine a local diagnostic indicator for the local patient, wherein the local diagnostic indicator is provided from the global data center to the local autonomous cell, and wherein the local autonomous cell and the global data center communicate using airmail, courier mail, e-mail, or other electronic data transfer methods.

As used in this specification and the appended claims, the singular forms "a", "an", and "the" include plural references unless the context clearly dictates otherwise. Any reference to "or" herein is intended to encompass "and/or" unless otherwise stated.

Reference has been made to embodiments of the disclosed invention. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A method for diagnosing diseases in animal patients comprising:

providing a set of global data to a global data center, including data from one or more tissue diffractometers;

training, by one or more processors, a machine learning algorithm, based on the set of global data, to generate a plurality of diagnostic indicators for assessment of physiological or pathological conditions;

categorizing, by the one or more processors and the trained machine learning algorithm, the set of global data into data clusters, where each data cluster is associated with a diagnostic indicator of the plurality of diagnostic indicators for a diagnosis of a disease;

measuring a local measurement data of a biological tissue of a patient using measurement equipment of a local autonomous cell, wherein the patient is an animal, the measurement equipment is a diffractometer configured to perform X-ray scattering measurements of a molecular structure of the biological tissue to collect diffraction pattern data related to ordering of the biological tissue, and the diffraction pattern data comprises a scattering pattern;

communicating the local measurement data and patient data from the local autonomous cell to the global data center;

pre-processing the local measurement data, by the one or more processors and the trained machine learning algorithm, to denoise, segment, mask, and/or enhance edges and/or features of the local measurement data;

processing the pre-processed local measurement data and comparing the processed local measurement data with the data clusters to determine one of the diagnostic indicators, wherein processing and comparing are performed by the one or more processors and the trained machine learning algorithm by operating upon the diffraction pattern data, and the diagnostic indicator includes a diagnosis that the patient has a disease; and communicating the diagnostic indicator from the global data center to the local autonomous cell to be displayed on a user interface of a computer screen.

2. The method of claim 1, wherein the measuring the local measurement data comprises measuring a sample comprising α-keratin or collagen.

3. The method of claim 1, wherein the measuring the local measurement data comprises in vivo or in vitro measurement of a sample comprising hair, nail, skin, wool, horns, hooves, or tissue of an internal organ.

4. The method of claim 1, wherein the set of global data is provided from a certain geographical region or nation.

5. The method of claim 1, wherein the one or more processors is in a cloud, and uses cloud computing to process data using a distributed network of computers.

6. The method of claim 1, wherein the global data center comprises the one or more processors.

7. The method of claim 1, further comprising an analytical center in communication with the global data center, wherein the analytical center comprises the one or more processors.

8. The method of claim 1, further comprising:

measuring a plurality of local measurement data of a plurality of patients using a plurality of measurement equipment of a plurality of local autonomous cells, wherein:

the local measurement data is one of the plurality of local measurement data;

the patient is one of the plurality of patients;

the measurement equipment is one of the plurality of measurement equipment;

the local autonomous cell is one of the plurality of local autonomous cells; and a plurality of patient data is associated with the plurality of patients;

communicating the plurality of local measurement data and the plurality of patient data from the plurality of local autonomous cells to the global data center;

processing the plurality of local measurement data using the one or more processors, wherein the processing is performed by the machine learning algorithm that determines a plurality of diagnostic indicators for the plurality of patients; and communicating the plurality of diagnostic indicators from the global data center to the plurality of local autonomous cells.

9. The method of claim 8, wherein local autonomous cells of the plurality of local autonomous cells are in different geographic locations.

10. The method of claim 1, further comprising providing a biological tissue sample from the patient to the local autonomous cell to be measured using the measurement equipment.

11. The method of claim 10, wherein the biological tissue sample comprises one or more of a surgical sample, a resection sample, a pathology sample, or a biopsy sample.

12. The method of claim 10, wherein the biological tissue sample comprises one or more of hair, nail, skin, or tissue of an internal organ.

13. The method of claim 10, wherein the providing a biological tissue sample from the patient to the local autonomous cell comprises the patient or a veterinary services provider of the patient using a second user interface to input the patient data and sending the biological tissue sample by mail.

14. The method of claim 1, wherein the communicating the local measurement data and the patient data from the local autonomous cell to the global data center is done by an owner of the patient or a veterinary services provider of the patient using a second user interface.

15. The method of claim 1, further comprising communicating the diagnostic indicator from the local autonomous cell to an owner of the patient or a veterinary services provider of the patient using the user interface.

16. The method of claim 1, further comprising encrypting the local measurement data and the patient data using a data encryption device coupled to the measurement equipment, wherein the communicating the local measurement data and the patient data from the local autonomous cell to the global data center comprises communicating the encrypted local measurement data and encrypted the patient data from the local autonomous cell to the global data center.

17. The method of claim 1, wherein the global data center further comprises a global database stored on a central server or in a cloud, wherein the global database comprises the set of global data.

18. The method of claim 1, further comprising depersonalizing the local measurement data, the patient data, or any combination thereof before communicating the local measurement data and the patient data from the local autonomous cell to the global data center, wherein the communicating the local measurement data and the patient data from the local autonomous cell to the global data center comprises communicating the depersonalized local measurement data and the depersonalized patient data from the local autonomous cell to the global data center.

19. The method of claim 18, wherein a key for mapping the depersonalized local measurement data, the patient data, or any combination thereof is stored in a local institutional database or in an individual personal file of the patient.

20. The method of claim 1, wherein the patient data comprises descriptions or data related to symptoms of the patient comprising one or more of sleep disorders, insomnia, sudden awakenings, somnambulism, apnea, disorders of cerebral circulation, electroencephalogram (EEG) data, sudden convulsions and fainting, headaches and dizziness, and traumatic brain injuries.

21. The method of claim 1, wherein the diagnostic indicator relates to one of more of breast cancer, brain cancer, bone cancer, lung cancer, cervical cancer, bladder cancer, head cancer, neck cancer, kidney cancer, intestinal cancer, liver cancer, ovarian cancer, pancreatic cancer, prostate cancer, skin cancer, throat cancer, oral cancer, vaginal cancer, sinus tachycardia of a heart, atrial extra-systoles, ventricular extra-systoles, acute myocardial infarction, heart valve defect, cardiomyopathy, ventricular hypertrophy, heart failure, arrhythmia, atrial fibrillation of the heart, pericarditis, bradycardia of the heart, myocarditis, ischemic stroke, neurological stroke, cognitive decline, glioblastoma, extracerebral tumors, bacterial endocarditis (inflammation of an inner lining of the heart), and meningococcal meningitis (inflammation of the membranes of a brain and spinal cord).

22. The method of claim 1, wherein the communicating the local measurement data and the patient data from the local autonomous cell to the global data center is done by mail, airmail, courier mail or e-mail.

23. The method of claim 1, wherein the communicating the local measurement data and the patient data from the local autonomous cell to the global data center or the communicating the diagnostic indicator from the global data center to the local autonomous cell occurs about once per day, or about once per week, or about once per month on average.

* * * * *